(12) United States Patent
Kikawa et al.

(10) Patent No.: US 7,982,880 B2
(45) Date of Patent: Jul. 19, 2011

(54) OPTICAL IMAGE MEASUREMENT DEVICE

(75) Inventors: Tsutomu Kikawa, Tokyo (JP); Hiroaki Okada, Tokyo (JP); Takefumi Hayashi, Tokyo (JP); Hisashi Tsukada, Tokyo (JP); Yasufumi Fukuma, Tokyo (JP)

(73) Assignee: Kabushiki Kaisha Topcon, Itabashi-ku (JP)

(*) Notice: Subject to any disclaimer, the term of this patent is extended or adjusted under 35 U.S.C. 154(b) by 0 days.

(21) Appl. No.: 12/659,869

(22) Filed: Mar. 24, 2010

(65) Prior Publication Data

US 2010/0188502 A1 Jul. 29, 2010

Related U.S. Application Data

(62) Division of application No. 11/962,196, filed on Dec. 21, 2007, now Pat. No. 7,777,893.

(30) Foreign Application Priority Data

Dec. 26, 2006 (JP) .................. 2006-349886

(51) Int. Cl.
*G01B 9/02* (2006.01)
(52) U.S. Cl. ...................... 356/479; 356/497
(58) Field of Classification Search ............. 356/479, 356/497
See application file for complete search history.

(56) References Cited

U.S. PATENT DOCUMENTS

| 2004/0233457 A1 | 11/2004 | Podoleanu et al. |
| 2005/0140984 A1 | 6/2005 | Hitzenberger |
| 2005/0254061 A1* | 11/2005 | Alphonse .................. 356/479 |

FOREIGN PATENT DOCUMENTS

| DE | 4309056 A1 | 9/1994 |
| JP | 11-325849 A | 11/1999 |
| JP | 2003-000543 A | 1/2003 |
| WO | WO-92/19930 A1 | 11/1992 |
| WO | WO-2005/047813 A1 | 5/2005 |

OTHER PUBLICATIONS

European Search Report dated Jun. 18, 2009, issued on the corresponding European application No. 07024818.2.

* cited by examiner

*Primary Examiner* — Tarifur Chowdhury
*Assistant Examiner* — Jonathon D Cook
(74) *Attorney, Agent, or Firm* — Edwards Angell Palmer & Dodge LLP

(57) ABSTRACT

A fundus oculi observation device acts as an optical image measurement device capable of measuring an OCT image such as a tomographic image of a fundus oculi, or the like, and is configured so as to calculate the signal level of the formed OCT image, determine whether the signal level exceeds a threshold value, and change the position of a reference mirror so that the signal level is determined to exceed the threshold value.

2 Claims, 12 Drawing Sheets

OPTICAL IMAGE MEASUREMENT DEVICE

This application is a divisional application of U.S. application Ser. No. 11/962,196, filed Dec. 21, 2007, and claims the right of priority under 35 U.S.C. §119 based on Japanese Patent Application No. 2006-349886 filed Dec. 26, 2006, which is hereby incorporated by reference herein in its entirety as if fully set forth herein.

BACKGROUND OF THE INVENTION

1. Field of the Invention

The present invention relates to an optical image measurement device configured to apply a light beam to a measurement subject and form an image of the surface morphology or internal morphology of the measurement subject by using a reflected light or a transmitted light.

2. Description of the Related Art

In recent years, attention has been focused on an optical image measurement technology of forming an image showing the surface morphology or internal morphology of a measurement subject by using a light beam from a laser light source or the like. Because this optical image measurement technology does not have invasiveness to human bodies unlike an X-ray CT device, it is particularly expected to further use this technology in the medical field.

Japanese Unexamined Patent Application Publication JP-A 11-325849 discloses an optical image measurement device having a configuration that: a measuring arm scans an object through a rotary deflection mirror (Galvano mirror); a reference mirror is disposed to a reference arm; an interferometer is used at the outlet so that the intensity of light appearing from interference of light fluxes from the measuring arm and the reference arm is analyzed by a spectrometer; and a device gradually changing the light flux phase of the reference light in non-continuous values is disposed to the reference arm.

The optical image measurement device of JP-A 11-325849 uses a method of so-called "Fourier Domain Optical Coherence Tomography (OCT)" based on technology of German Patent Application Publication DE4309056A1. That is to say, a beam of a low-coherence light is applied to a measurement subject, the spectrum intensity distribution of a reflected light is obtained, and the obtained distribution is subjected to Fourier transformation, whereby an image of the morphology of the measurement subject in a depth direction (z-direction) is formed.

Furthermore, the optical image measurement device described in JP-A 11-325849 is provided with a Galvano mirror that scans with an optical beam (signal light), whereby it is possible to form an image of a desired measurement region of a measurement subject. Because this optical image measurement device is configured to scan with a light beam only in one direction (x-direction) orthogonal to the z-direction, a formed image is a 2-dimensional cross-sectional image of the depth direction (z-direction) along the light beam scanning direction (x-direction).

Besides, Japanese Unexamined Patent Application Publication JP-A 2003-543 discloses a configuration in which the aforementioned optical image measurement device is applied to the field of ophthalmology.

An optical image measurement device forms an image by measuring a depth almost the same as the length of a reference arm (the optical path length of a reference light). Therefore, in order to capture an image of a desired depth position, it is necessary to place a reference mirror at a position corresponding to the depth position. Considering the use of a low-coherence light, alignment of the reference mirror, namely, alignment of the measurement position in the depth direction must be conducted precisely.

Further, in an optical image measurement device, the measurement sensitivity is the most favorable at a depth position that coincides with the optical path length of the reference light (origin of the z-direction), and the measurement sensitivity becomes lower as it is distant from the origin. Also from this aspect, it is understood that alignment of the measurement position in the depth direction needs precision.

However, the conventional optical image measurement devices have a problem in that it is impossible to easily align the measurement position in the depth direction of a measurement subject.

SUMMARY OF THE INVENTION

The present invention has been devised to solve the problem as described above, and an object of the present invention is to provide an optical image measurement device capable of easily aligning a measurement position in the depth direction of a measurement subject.

In a first aspect of the present invention, an optical image measurement device comprises: a light source configured to emit a low-coherence light; an interference-light generator configured to generate an interference light by splitting the emitted low-coherence light into a signal light heading toward a measurement subject and a reference light heading toward a reference object, and superimposing the signal light passed through the measurement subject and the reference light passed through the reference object; a changer configured to change a difference in optical path length between the signal light and the reference light; a detector configured to detect the generated interference light; an image forming part configured to form an image based on the result of the detection by the detector; an analyzer configured to analyze the formed image to calculate a signal level or a ratio of a signal level and a noise level of an image, and determine whether the signal level or the ratio of the signal level and the noise level exceeds a threshold value; and a controller configured to control the changer to change the difference in optical path length so that the analyzer determines the difference to exceed the threshold value.

In a second aspect of the present invention, an optical image measurement device comprises: a light source configured to emit a low-coherence light; an interference-light generator configured to generate a interference light by splitting the emitted low-coherence light into a signal light heading toward a measurement subject and a reference light heading toward a reference object, and superimposing the signal light passed through the measurement subject and the reference light passed through the reference object; a changer configured to change a difference in optical path length between the signal light and the reference light; a detector configured to detect the generated interference light; an image forming part configured to form an image within a predetermined frame based on the result of the detection by the detector; and a controller configured to control the changer to change the difference in optical path length so that a partial image corresponding to a predetermined depth position of the measurement subject in the formed image is placed in a specific position within the predetermined frame.

BRIEF DESCRIPTION OF THE DRAWINGS

FIG. 8A shows one example of a scanning pattern of the signal light when a fundus oculi is seen from the incident side of the signal light to an eye. FIG. 8B shows one example of an arrangement pattern of scanning points on each scanning line.

DETAILED DESCRIPTION OF THE PREFERRED EMBODIMENT

Figure 1:
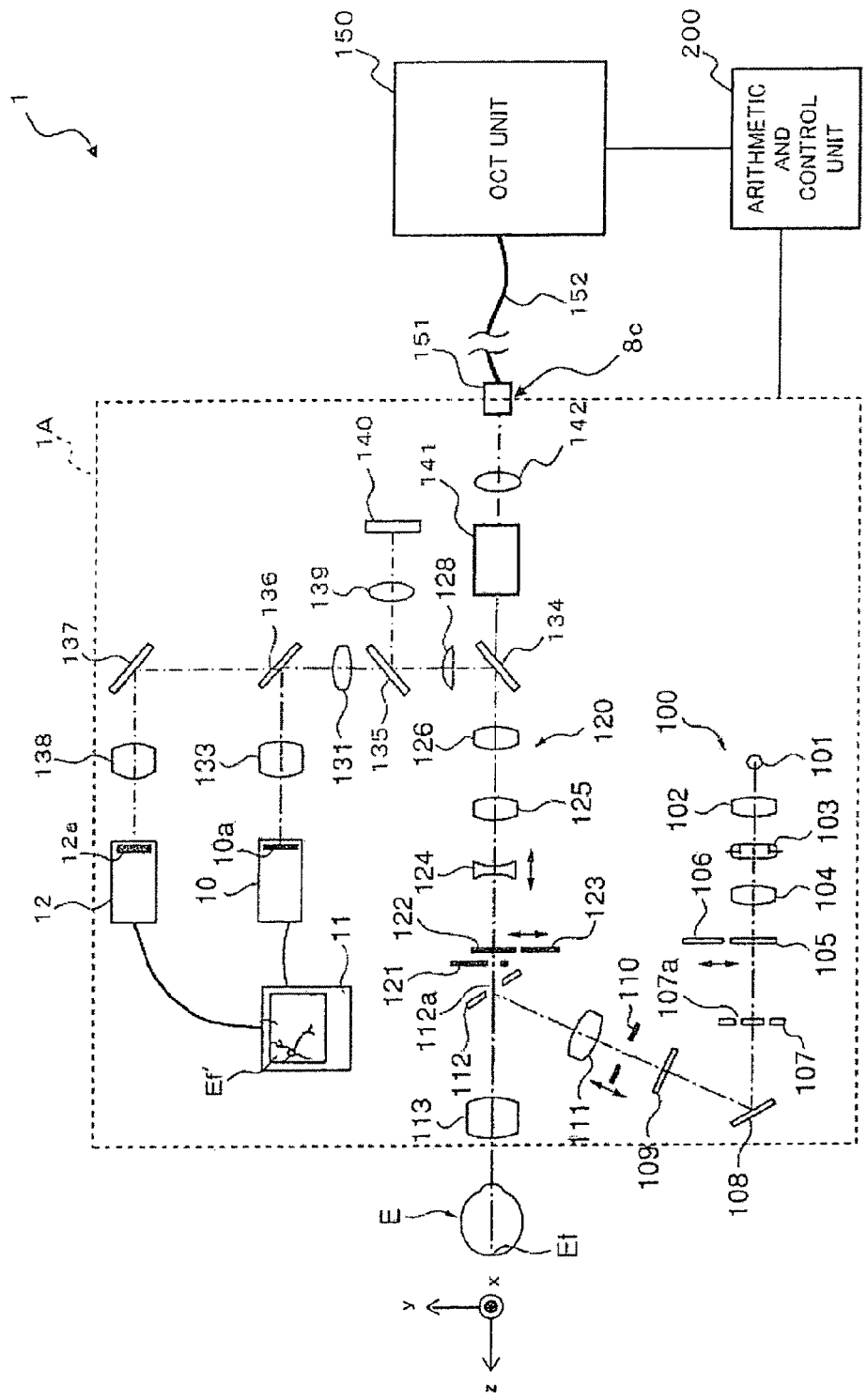
FIG. 1 is a schematic configuration diagram showing one example of the entire configuration in a preferred embodiment of a device related to the present invention.

One example of a preferred embodiment of an optical image measurement device according to the present invention will be described in detail referring to the drawings.

[Configuration of Device]

Figure 2:
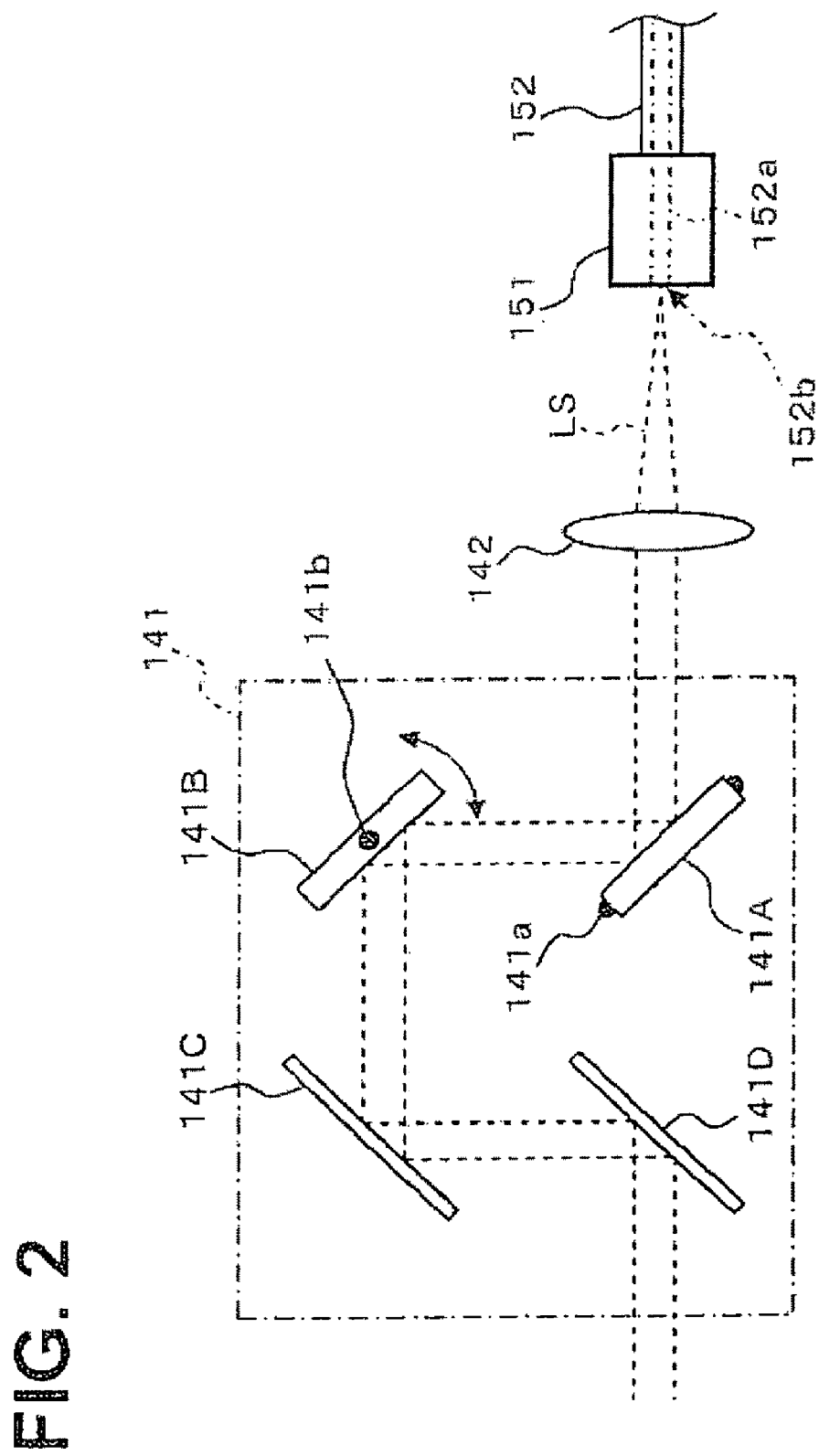
FIG. 2 is a schematic configuration diagram showing one example of the configuration of a scan unit installed in a retinal camera unit in the preferred embodiment of the device related to the present invention.
Figure 3:
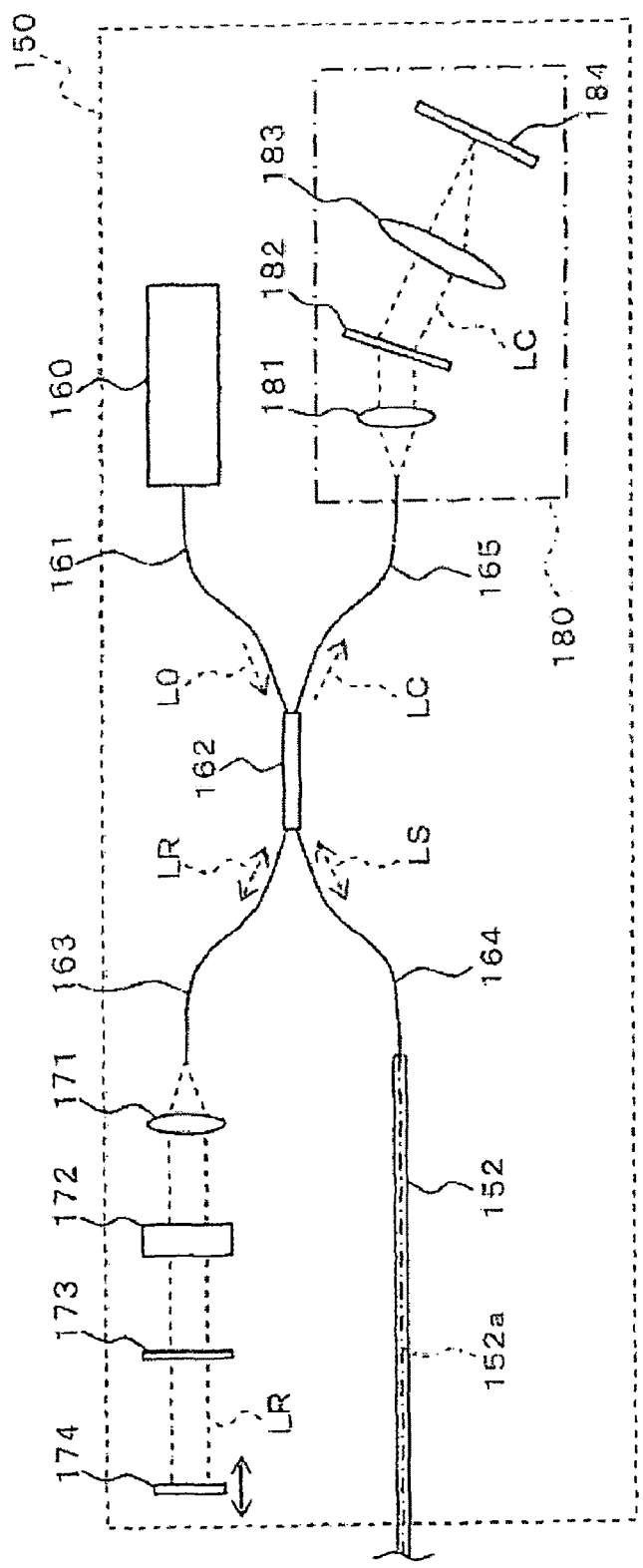
FIG. 3 is a schematic configuration diagram showing one example of the configuration of an OCT unit in the preferred embodiment of the device related to the present invention.
Figure 4:
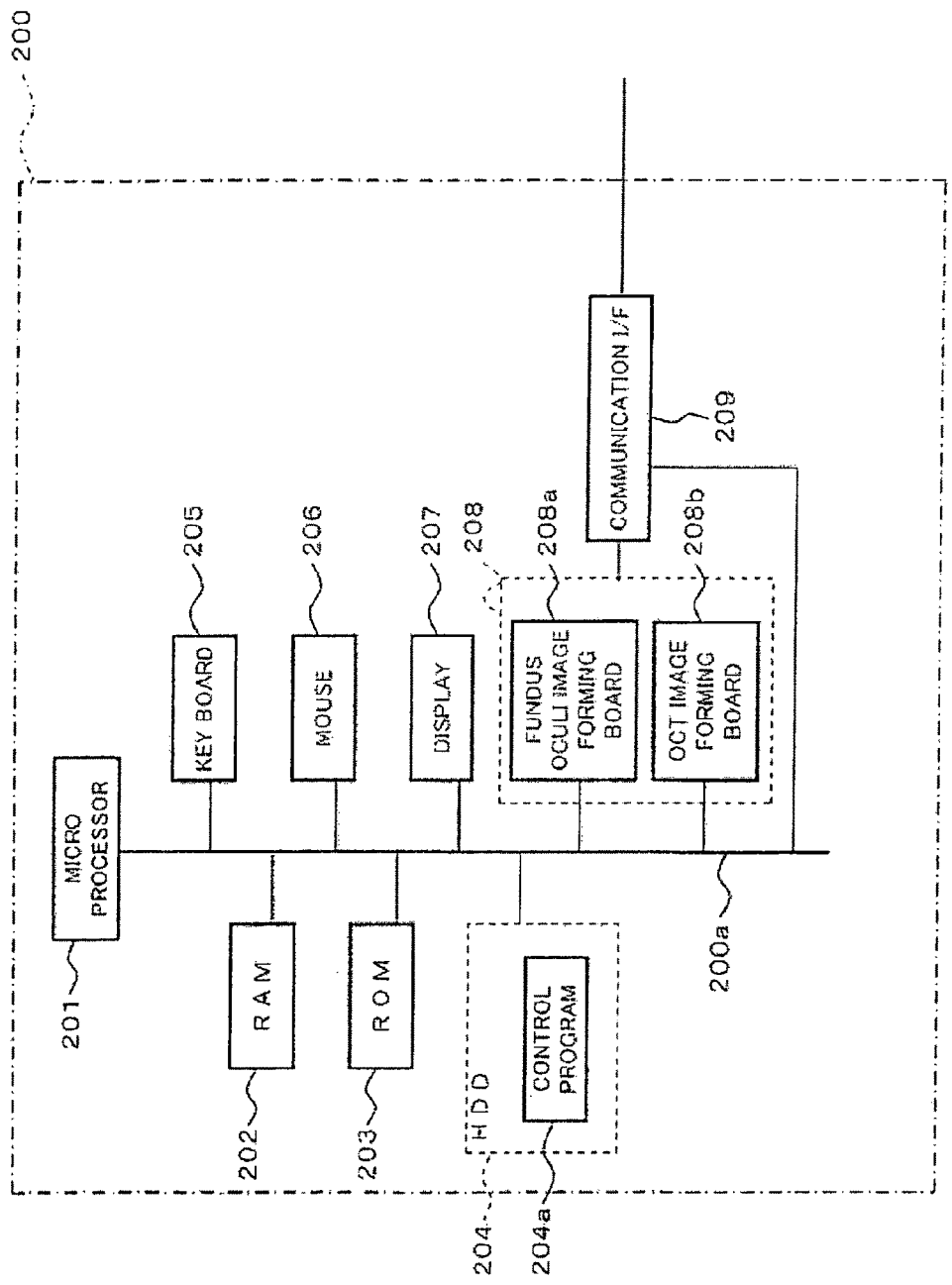
FIG. 4 is a schematic block diagram showing one example of the hardware configuration of an arithmetic control unit in the preferred embodiment of the device related to the present invention.
Figure 5:
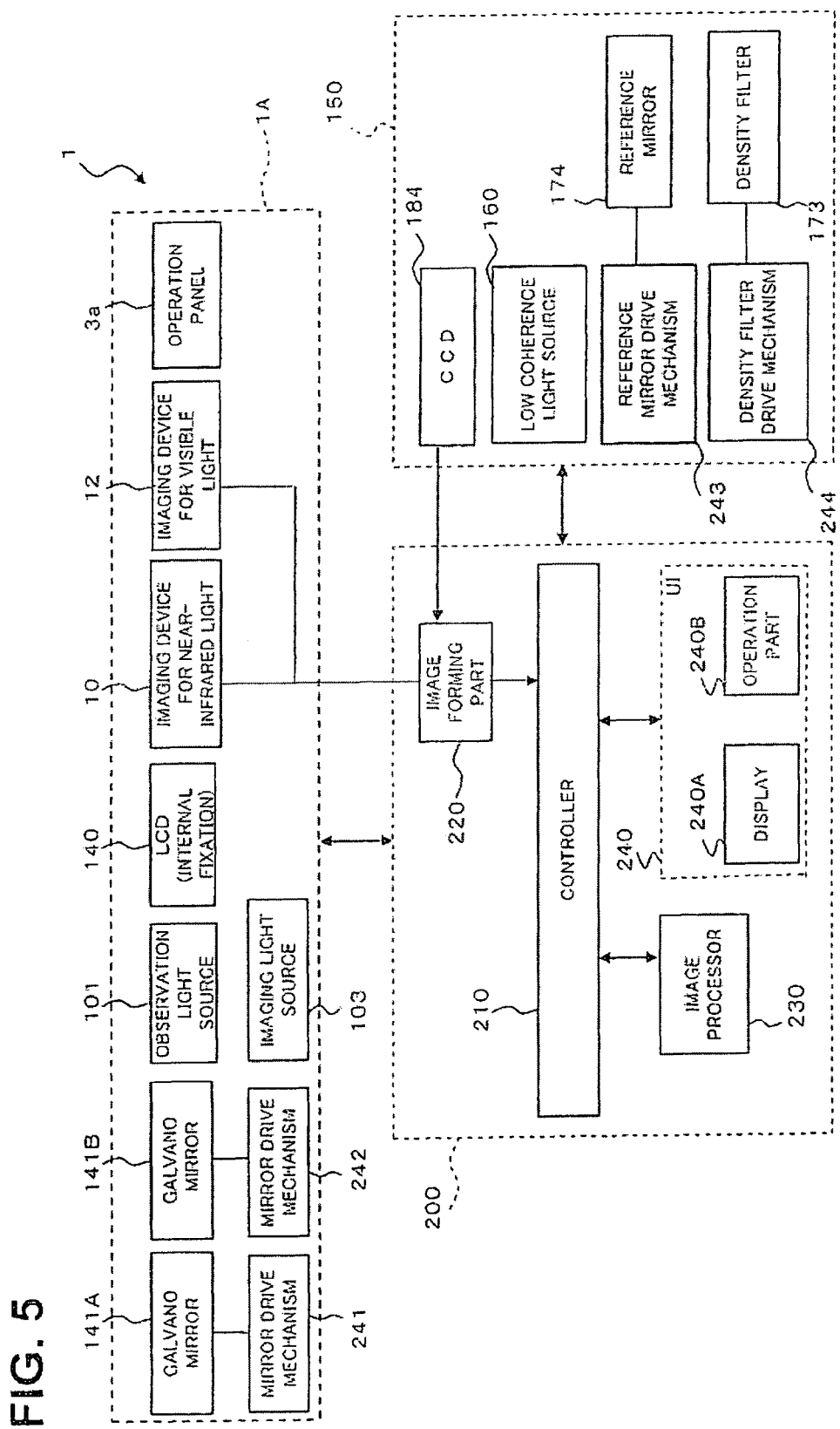
FIG. 5 is a schematic block diagram showing one example of the configuration of a control system in the preferred embodiment of the device related to the present invention.
Figure 6:
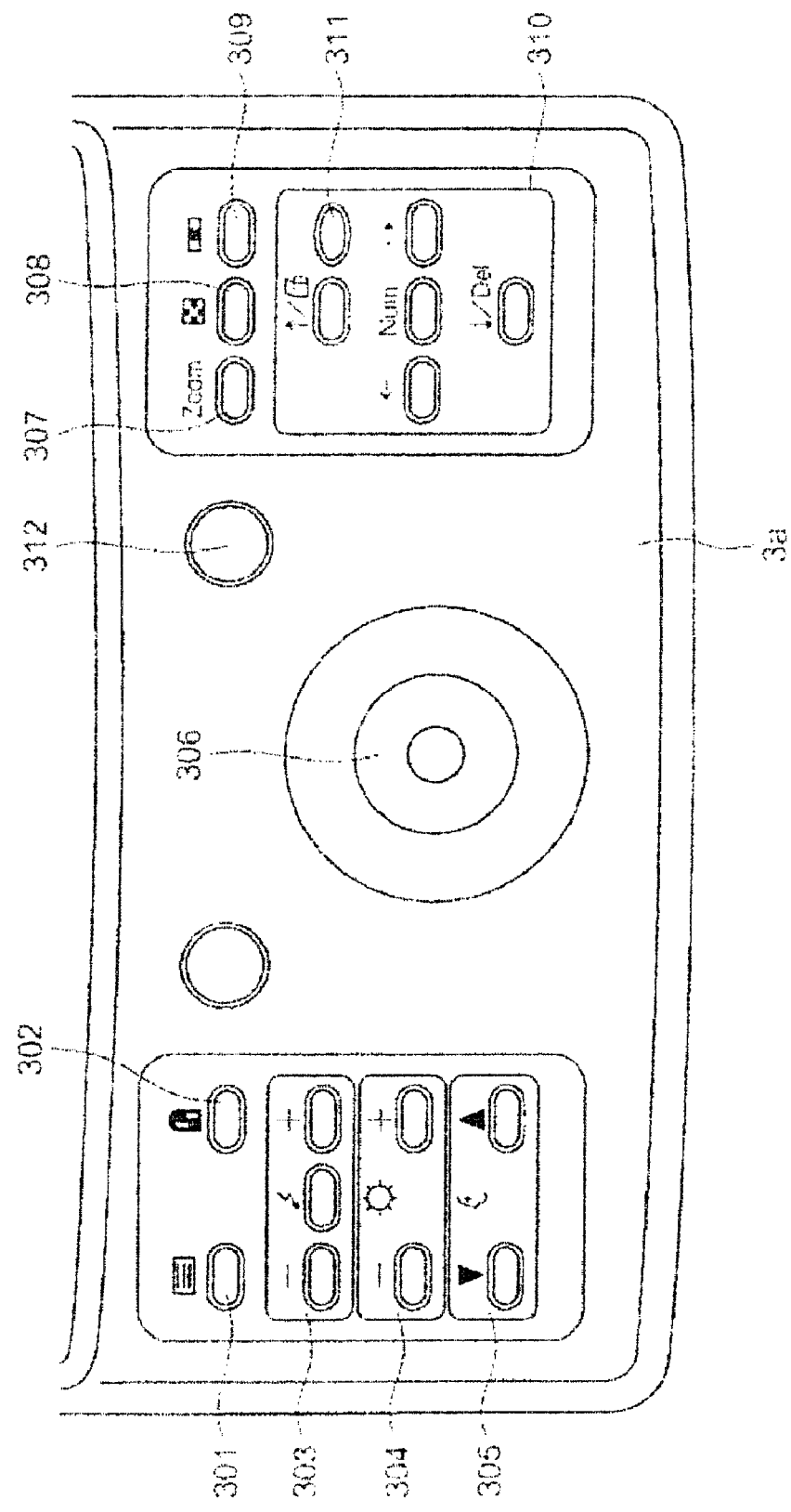
FIG. 6 is a schematic view showing one example of the appearance of an operation panel in the preferred embodiment of the device related to the present invention.
Figure 7:
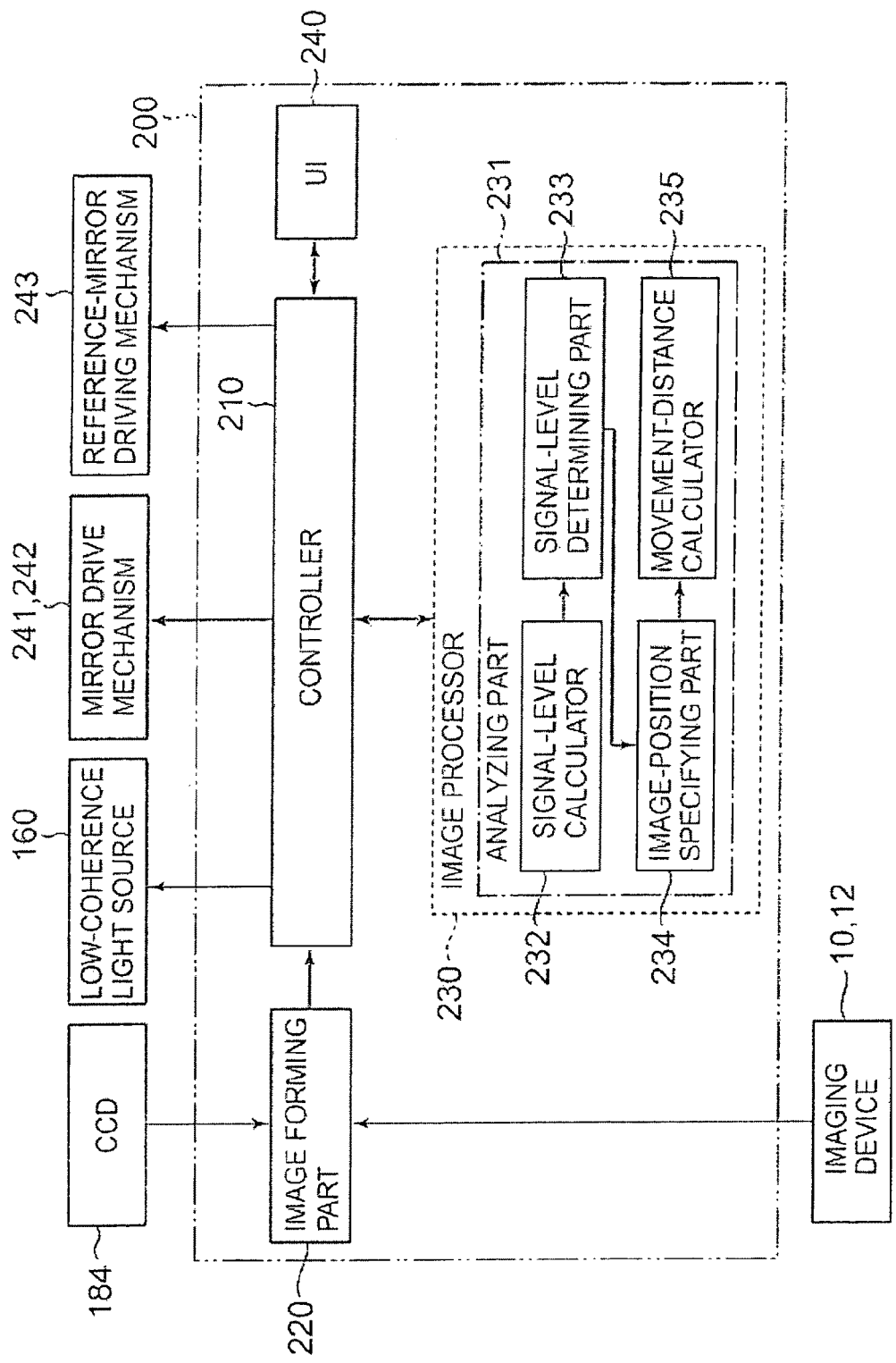
FIG. 7 is a schematic block diagram showing one example of the functional configuration of the arithmetic control unit in the preferred embodiment of the device related to the present invention.

First, referring to FIGS. 1 through 7, the configuration of the optical image measurement device according to a first embodiment of the present invention will be described. FIG. 1 shows one example of the entire configuration of a fundus oculi observation device 1 having a function as the optical image measurement device according to this embodiment. FIG. 2 shows one example of the configuration of a scan unit 141 in a retinal camera unit 1A. FIG. 3 shows one example of the configuration of an OCT unit 150. FIG. 4 shows one example of the hardware configuration of an arithmetic control unit 200. FIG. 5 shows one example of the configuration of a control system of the fundus oculi observation device 1. FIG. 6 shows one example of the configuration of an operation panel 3a disposed to the retinal camera unit 1A. FIG. 7 shows one example of the configuration of a control system of the arithmetic control unit 200.

[Entire Configuration]

The fundus oculi observation device 1 related to this embodiment comprises a retinal camera unit 1A, an OCT unit 150, and an arithmetic control unit 200 as shown in FIG. 1. The retinal camera unit 1A has almost the same optical system as the conventional retinal cameras for photographing 2-dimensional images of the fundus oculi surface. The OCT unit 150 houses an optical system that functions as an optical image measurement device. The arithmetic control unit 200 is equipped with a computer for executing various types of arithmetic processes, control processes, or the like.

To the OCT unit 150, one end of a connection line 152 is attached. A connector part 151 for connecting the connection line 152 to the retinal camera unit 1A is attached to the other end of the connection line 152. A conductive optical fiber runs through inside the connection line 152. Thus, the OCT unit 150 and the retinal camera unit 1A are optically connected via the connection line 152.

Configuration of Retinal Camera Unit

The retinal camera unit 1A is used for forming a 2-dimensional image of the surface of a fundus oculi of an eye, based on optically obtained data (data detected by the imaging devices 10 and 12). Herein, the "2-dimensional image of the surface of the fundus oculi" refers to a color or monochrome image of the surface of the fundus oculi having been photographed, a fluorescent image (a fluorescein angiography image, an indocyanine green fluorescent image, etc.), and the like. As well as the conventional retinal camera, the retinal camera unit 1A is provided with an illumination optical system 100 that illuminates a fundus oculi Ef of an eye E, and an imaging optical system 120 that guides the fundus oculi reflection light of the illumination light to the imaging device 10.

Although the details will be described later, the imaging device 10 in the imaging optical system 120 of this embodiment detects the illumination light having a wavelength in the near-infrared region. Moreover, this imaging optical system 120 is further provided with the imaging device 12 for detecting the illumination light having a wavelength in the visible region. Moreover, this imaging optical system 120 guides a signal light coming from the OCT unit 150 to the fundus oculi Ef, and guides the signal light passed through the fundus oculi Ef to the OCT unit 150.

The illumination optical system 100 comprises: an observation light source 101; a condenser lens 102; an imaging light source 103; a condenser lens 104; exciter filters 105 and 106; a ring transparent plate 107; a mirror 108; an LCD (Liquid Crystal Display) 109; an illumination diaphragm 110; a relay lens 111; an aperture mirror 112; and an objective lens 113.

The observation light source 101 emits an illumination light having a wavelength of the visible region included in a range of, for example, about 400 nm thorough 700 nm. Moreover, the imaging light source 103 emits an illumination light having a wavelength of the near-infrared region included in a range of, for example, about 700 nm through 800 nm. The near-infrared light emitted from this imaging light source 103 is set so as to have a shorter wavelength than the light used by the OCT unit 150 (described later).

Further, the imaging optical system 120 comprises: an objective lens 113; an aperture mirror 112 (an aperture 112a thereof); an imaging diaphragm 121; barrier filters 122 and 123; a variable magnifying lens 124; a relay lens 125; an imaging lens 126; a dichroic mirror 134; a field lens 128; a half mirror 135; a relay lens 131; a dichroic mirror 136; an imaging lens 133; the imaging device 10 (image pick-up element 10a); a reflection mirror 137; an imaging lens 138; the imaging device 12 (image pick-up element 12a); a lens 139; and an LCD 140.

The dichroic mirror 134 is configured to reflect the fundus oculi reflection light (having a wavelength included in a range of about 400 nm through 800 nm) of the illumination light from the illumination optical system 100, and transmit a signal light LS (having a wavelength included in a range of, for example, about 800 nm through 900 nm; described later) from the OCT unit 150.

Further, the dichroic mirror 136 is configured to transmit the illumination light having a wavelength of the visible region from the illumination optical system 100 (a visible light having a wavelength of about 400 nm through 700 nm emitted from the observation light source 101), and reflect the illumination light having a wavelength of the near-infrared region (a near-infrared light having a wavelength of about 700 nm through 800 nm emitted from the imaging light source 103).

On the LCD 140, a fixation target (internal fixation target) or the like for fixing the eye E is displayed. The light from this LCD 140 is reflected by the half mirror 135 after being converged by the lens 139, and is reflected by the dichroic mirror 136 through the field lens 128. Then, the light passes through the imaging lens 126, the relay lens 125, the variable magnifying lens 124, the aperture mirror 112 (aperture 112a thereof), the objective lens 113 and the like, and enters the eye E. Consequently, an internal fixation target or the like is projected in the fundus oculi Ef of the eye E.

The image pick-up element 10a is an image pick-up element such as a CCD (Charge Coupled Device) and a CMOS (Complementary metal Oxide Semiconductor) installed in the imaging device 10 such as a TV camera, and is particularly used for detecting light having a wavelength of the near-infrared region. In other words, the imaging device 10 is an infrared TV camera for detecting near-infrared light. The imaging device 10 outputs video signals as a result of detection of the near-infrared light.

A touch panel monitor 11 displays a 2-dimensional image (a fundus oculi image Ef') of the surface of the fundus oculi Ef, based on the video signals. The video signals are sent to the arithmetic control unit 200, and the fundus oculi image is displayed on the display (described later).

At the time of imaging of the fundus oculi by the imaging device 10, for example, the illumination light emitted from the imaging light source 103 of the illumination optical system 100 and having a wavelength of the near-infrared region is used.

On the other hand, the image pick-up element 12a is an image pick-up element such as a CCD and a CMOS installed in the imaging device 12 such as a TV camera, and is particularly used for detecting light having a wavelength of the visible region (that is, the imaging device 12 is a TV camera for detecting visible light). The imaging device 12 outputs video signals as a result of detection of the visible light.

The touch panel monitor 11 displays a 2-dimensional image (fundus oculi image Ef') of the surface of the fundus oculi Ef, based on the video signals. The video signals are sent to the arithmetic control unit 200, and the fundus oculi image Ef' is displayed on the display (described later).

At the time of imaging of the fundus oculi by the imaging device 12, for example, the illumination light emitted from the observation light source 101 of the illumination optical system 100 and having a wavelength of the visible region is used.

The retinal camera unit 1A is provided with a scan unit 141 and a lens 142. The scan unit 141 includes a component for scanning at an application position of the fundus oculi Ef with light emitted from the OCT unit (signal light LS; described later).

The lens 142 makes the signal light LS guided from the OCT unit 150 through the connection line 152 enter the scan unit 141 in the form of a parallel light flux. Moreover, the lens 142 acts so as to converge the fundus oculi reflection light of the signal light LS passed through the scan unit 141.

FIG. 2 shows one example of a specific configuration of the scan unit 141. The scan unit 141 comprises Galvano mirrors 141A and 141B, and reflection mirrors 141C and 141D.

The Galvano mirrors 141A and 141B are reflection mirrors disposed so as to be rotatable about rotary shafts 141a and 141b, respectively. The Galvano mirrors 141A and 141B are rotated about the rotary shafts 141a and 141b, respectively, by a drive mechanism described later (mirror drive mechanisms 241 and 242 shown in FIG. 5), whereby the orientations of reflection surfaces thereof (faces reflecting the signal light LS), namely, the positions of the Galvano mirrors 141A and 141B are changed, respectively.

The rotary shafts 141a and 141b are arranged so as to be orthogonal to each other. In FIG. 2, the rotary shaft 141a of the Galvano mirror 141A is arranged in parallel to the paper face of FIG. 2, whereas the rotary shaft 141b of the Galvano mirror 141B is arranged so as to be orthogonal to the paper face of FIG. 2.

That is to say, the Galvano mirror 141B is formed so as to be rotatable in the directions indicated by an arrow pointing in both directions in FIG. 2, whereas the Galvano mirror 141A is formed so as to be rotatable in the directions orthogonal to the arrow pointing in both the directions. Consequently, the pair of Galvano mirrors 141A and 141B act so as to change the reflecting directions of the signal light LS to directions orthogonal to each other. As seen from FIGS. 1 and 2, scan with the signal light LS is performed in the x direction when the Galvano mirror 141A is rotated, and scan with the signal light LS is performed in the y direction when the Galvano mirror 141B is rotated.

The signal lights LS reflected by the Galvano mirrors 141A and 141B are reflected by reflection mirrors 141C and 141D, thereby traveling in the same directions as having entered into the Galvano mirror 141A.

As described before, the conductive optical fiber 152a runs through the inside of the connection line 152, and an end face 152b of the optical fiber 152a is arranged facing the lens 142. The signal light LS emitted from this end face 152b travels while expanding its beam diameter toward the lens 142. The light is converged into a parallel light flux by this lens 142. On the contrary, the signal light LS passed through the fundus oculi Ef is converged toward the end face 152b by the lens 142, and guided to the optical fiber 152a.

Configuration of OCT Unit

Next, the configuration of the OCT unit 150 will be described referring to FIG. 3. The OCT unit 150 is a device configured to form a tomographic image of the fundus oculi based on optically obtained data (data detected by a CCD 184 described later).

The OCT unit 150 has almost the same optical system as the conventional optical image measurement device. That is, the OCT unit 150 has: an interferometer that splits the light emitted from the light source into a reference light and a signal light and generates interference-light by superposing the reference light passed through a reference object and the signal light passed through a measurement object (fundus oculi Ef); and a part configured to detect this interference-light and output signals as the result of the detection (detection signals) toward the arithmetic control unit 200. The arithmetic control unit 200 forms a tomographic image of the measurement object (fundus oculi Ef), by analyzing the detection signals.

A low-coherence light source 160 is composed of a broadband light source, such as a super luminescent diode (SLD) and a light emitting diode (LED), configured to emit a low-coherence light L0. This low-coherence light L0 is, for example, a light that has a wavelength of the near-infrared region and has a time-wise coherence length of approximately several tens of micrometers. The low-coherence light source 160 corresponds to one example of the "light source" of the present invention.

The low-coherence light L0 has a longer wavelength than the illumination light (wavelength: about 400 nm through 800 nm) of the retinal camera unit 1A, for example, a wavelength included in a range of about 800 nm through 900 nm.

The low-coherence light L0 emitted from the low-coherence light source 160 is guided to an optical coupler 162 through an optical fiber 161. The optical fiber 161 is composed of, for example, a single mode fiber or a PM (Polarization maintaining) fiber. The optical coupler 162 splits this low-coherence light L0 into a reference light LR and the signal light LS.

Although the optical coupler 162 acts as both a part (splitter) for splitting light and a part (coupler) for superposing lights, it will be herein referred to as an "optical coupler" idiomatically.

The reference light LR generated by the optical coupler 162 is guided by an optical fiber 163 composed of a single mode fiber or the like, and emitted from the end face of the fiber. The emitted reference light LR is converged into a parallel light flux by a collimator lens 171, passed through a glass block 172 and a density filter 173, and then reflected by a reference mirror 174 (reference object).

The reference light LR reflected by the reference mirror 174 is converged to the fiber end face of the optical fiber 163 by the collimator lens 171 again through the density filter 173 and the glass block 172. The converged reference light LR is guided to the optical coupler 162 through the optical fiber 163.

The glass block 172 and the density filter 173 act as a delaying part for making the optical path lengths (optical distances) of the reference light LR and the signal light LS coincide, and also as a dispersion correction part for making the dispersion characteristics of the reference light LR and the signal light LS coincide.

Further, the density filter 173 also acts as a dark filter for reducing the amount of the reference light, and is composed of a rotating ND (neutral density) filter, for example. This density filter 173 acts so as to change the reduction amount of the reference light LR by being rotary driven by a drive mechanism including a drive unit such as a motor (a density filter drive mechanism 244 described later; refer to FIG. 5). Consequently, it is possible to change the amount of the reference light LR contributing to generation of the interference-light LC.

Further, the reference mirror 174 is configured so as to move in the traveling direction (the direction of the arrow pointing both sides shown in FIG. 3) of the reference light LR. With this configuration, it is possible to ensure the optical path length of the reference light LR according to the axial length of the eye E, etc. Moreover, it is possible to capture an image of any depth position of the fundus oculi Ef, by moving the reference mirror 174. The reference mirror 174 is moved by a drive mechanism (a reference mirror driving mechanism 243 described later; refer to FIG. 5) including a driver such as a motor.

On the other hand, the signal light LS generated by the optical coupler 162 is guided to the end of the connection line 152 through an optical fiber 164 composed of a single mode fiber or the like. The conductive optical fiber 152a runs inside the connection line 152. Herein, the optical fiber 164 and the optical fiber 152a may be composed of a single optical fiber, or may be jointly formed by connecting the end faces of the respective fibers. In either case, it is sufficient as far as the optical fiber 164 and 152a are configured to be capable of transferring the signal light LS between the retinal camera unit 1A and the OCT unit 150.

The signal light LS is guided through the inside of the connection line 152 and led to the retinal camera unit 1A. Then, the signal light LS enters into the eye E through the lens 142, the scan unit 141, the dichroic mirror 134, the imaging lens 126, the relay lens 125, the variable magnifying lens 124, the imaging diaphragm 121, the aperture 112a of the aperture mirror 112, and the objective lens 113. The barrier filter 122 and 123 are retracted from the optical path in advance, respectively, when the signal light LS is made to enter the eye E.

The signal light LS having entered the eye E forms an image on the fundus oculi (retina) Ef and is then reflected. At this moment, the signal light LS is not only reflected on the surface of the fundus oculi Ef, but also scattered at the refractive index boundary after reaching the deep area of the fundus oculi Ef. As a result, the signal light LS passed through the fundus oculi Ef is a light containing information reflecting the state of the surface of the fundus oculi Ef and information reflecting the state of backscatter at the refractive index boundary of the deep area tissue of the fundus oculi Ef. This light may be simply referred to as "fundus oculi reflection light of the signal light LS."

The fundus oculi reflection light of the signal light LS travels reversely on the above path within the retinal camera unit 1A, and is converged at the end face 152b of the optical fiber 152a. Then, the signal light LS enters into the OCT unit 150 through the optical fiber 152a, and returns to the optical coupler 162 through the optical fiber 164.

The optical coupler 162 superimposes the signal light LS returning through the fundus oculi Ef and the reference light LR reflected by the reference mirror 174, thereby generating the interference-light LC. The generated interference-light LC is guided into a spectrometer 180 through an optical fiber 165 composed of a single mode fiber or the like.

Herein, although a Michelson-type interferometer is adopted in this embodiment, for instance, a Mach Zender type, etc. and any type of interferometer may be adopted appropriately. The "interference-light generator" related to the present invention comprises, for example, an optical coupler 162, optical members on the optical path of the signal light LS (i.e., optical members placed between the optical coupler 162 and the fundus oculi Ef), and optical members on the optical path of the reference light LR (i.e., optical members placed between the optical coupler 162 and the reference mirror 174), and specifically, comprises an interferometer equipped with the optical coupler 162, the optical fibers 163, 164, and the reference mirror 174.

The spectrometer 180 comprises a collimator lens 181, a diffraction grating 182, an image-forming lens 183, and a CCD 184. The diffraction grating 182 in this embodiment is a transmission-type diffraction grating that transmits light; however, needless to say, a reflection-type diffraction grating that reflects light may also be used. Moreover, needless to say, it is also possible to adopt, in place of the CCD 184, other photo-detecting elements.

The interference light LC having entered the spectrometer 180 is split (resolved into spectra) by the diffraction grating 182 after converged into a parallel light flux by the collimator lens 181. The split interference light LC forms an image on the image pick-up surface of the CCD 184 by the image-forming lens 183. The CCD 184 detects the respective spectra of the interference light LC and converts to electrical signals, and outputs the detection signals to the arithmetic control unit 200. The CCD 184 functions as the "detector" of the present invention.

Configuration of Arithmetic Control Unit

Next, the configuration of the arithmetic control unit 200 will be described. The arithmetic control unit 200 performs a process of analyzing detection signals inputted from the CCD 184 of the spectrometer 180 of the OCT unit 150 and forming a tomographic image of the fundus oculi Ef of the eye E. The analysis method is the same as the conventional technique of Fourier Domain OCT.

Further, the arithmetic control unit 200 performs a process of forming (image data of) a 2-dimensional image showing the state of the surface (retina) of the fundus oculi Ef, based on the video signals outputted from the imaging devices 10 and 12 of the retinal camera unit 1A.

Furthermore, the arithmetic control unit 200 executes control of each part of the retinal camera unit 1A and the OCT unit 150.

The arithmetic control unit 200 executes as control of the retinal camera unit 1A, for example: control of emission of illumination light by the observation light source 101 or the imaging light source 103; control of insertion/retraction operations of the exciter filters 105 and 106 or the barrier filters 122 and 123 to/from the optical path; control of the operation of a display device such as the LCD 140; control of shift of the illumination diaphragm 110 (control of the diaphragm value); control of the diaphragm value of the imaging diaphragm 121; and control of shift of the variable magnifying lens 124 (control of the magnification). Moreover, the arithmetic control unit 200 executes control of the operation of the Galvano mirrors 141A and 141B inside the scan unit 141 (operation of changing the directions of the reflection faces).

Further, the arithmetic control unit 200 executes as control of the OCT unit 150, for example: control of emission of the low-coherence light L0 by the low-coherence light source 160; control of shift of the reference mirror 174; control of the rotary operation of the density filter 173 (operation of changing the reduction amount of the reference light LR); and control of the accumulated time of the CCD 184.

One example of the hardware configuration of the arithmetic and control unit 200 that acts as described above will be described referring to FIG. 4.

The arithmetic and control unit 200 is provided with the same hardware configuration as that of a conventional computer. To be specific, the arithmetic and control unit 200 comprises: a microprocessor 201 (CPU, MPU, etc.), a RAM 202, a ROM 203, a hard disk drive (HDD) 204, a keyboard 205, a mouse 206, a display 207, an image forming board 208, and a communication interface (I/F) 209. These parts are connected via a bus 200a.

The microprocessor 201 comprises a CPU (Central Processing Unit), an MPU (Micro Processing Unit) or the like, and executes operations characteristic to this embodiment, by loading a control program 204a stored in the hard disk drive 204, onto the RAM 202.

Further, the microprocessor 201 executes control of each part of the device described above, various arithmetic processes, etc. Moreover, the microprocessor 201 executes control of each part of the device corresponding to an operation signal from the keyboard 205 or the mouse 206, control of a display process by the display 207, and control of a transmission/reception process of various data, control signals and so on by the communication interface 209.

The keyboard 205, the mouse 206 and the display 207 are used as user interfaces in the fundus oculi observation device 1. The keyboard 205 is used as, for example, a device for typing letters, figures, etc. The mouse 206 is used as a device for performing various input operations to the display screen of the display 207.

Further, the display 207 is any display device composed of an LCD, a CRT (Cathode Ray Tube) display or the like. The display 207 displays various images of the fundus oculi Ef formed by the fundus oculi observation device 1, and displays various screens such as an operation screen and a set-up screen.

The user interface of the fundus oculi observation device 1 is not limited to the above configuration, and may be configured by using any user interface having a function of displaying and outputting various information, and a function of inputting various information and operating the device, such as a track ball, a control lever, a touch panel type of LCD, and a control panel for ophthalmology examinations.

The image forming board 208 is a dedicated electronic circuit for a process of forming (image data of) images of the fundus oculi Ef of the eye E. This image forming board 208 is provided with a fundus oculi image forming board 208a and an OCT-image forming board 208b.

The fundus oculi image forming board 208a is a dedicated electronic circuit that operates to form image data of fundus oculi images based on the video signals from the imaging device 10 and the imaging device 12 of the retinal camera unit 1A.

Further, the OCT-image forming board 208b is a dedicated electronic circuit that operates to form image data of tomographic images of the fundus oculi Ef, based on the detection signals from the CCD 184 of the spectrometer 180 in the OCT unit 150.

By providing the image forming board 208, it is possible to increase the processing speed for forming image data of fundus oculi images and tomographic images.

The communication interface 209 performs a process of sending control signals from the microprocessor 201, to the retinal camera unit 1A or the OCT unit 150. Moreover, the communication interface 209 performs a process of receiving video signals from the imaging devices 10 and 12 of the retinal camera unit 1A and detection signals from the CCD 184 of the OCT unit 150, and inputting the signals to the image forming board 208. At this time, the communication interface 209 operates to input the video signals from the imaging devices 10 and 12, to the fundus oculi image forming board 208a, and input the detection signal from the CCD 184, to the OCT-image forming board 208b.

Further, in a case where the arithmetic and control unit 200 is connected to a network such as a LAN (Local Area Network) and the Internet, it is possible to configure so as to be capable of data communication via the network, by providing the communication interface 209 with a network adapter like a LAN card or communication equipment like a modem. In this case, by mounting a server accommodating the control program 204a on the network, and at the same time, configuring the arithmetic and control unit 200 as a client terminal of the server, it is possible to cause the fundus oculi observation device 1 to execute the operation according to the present invention.

Configuration of Control System

Next, the configuration of the control system of the fundus oculi observation device 1 will be described referring to FIG. 5 through FIG. 7. FIG. 5 is a block diagram showing a part related to the operations and processes according to the present invention particularly selected from among constituents composing the fundus oculi observation device 1. FIG. 6 shows one example of the configuration of the operation panel 3a disposed to the retinal camera unit 1A. FIG. 7 is a block diagram showing a detailed configuration of the arithmetic and control unit 200.

(Controller)

The control system of the fundus oculi observation device 1 is configured mainly having a controller 210 of the arithmetic and control unit 200 shown in FIG. 5. The controller 210 comprises the microprocessor 201, the RAM 202, the ROM 203, the hard disk drive 204 (control program 204a), and the communication interface 209.

The controller 210 executes the aforementioned controlling processes through the microprocessor 201 operating based on the control program 204a. In specific, for the retinal camera unit 1A, the controller 210 performs control of the mirror drive mechanisms 241 and 242 for changing the positions of the Galvano mirrors 141A and 141B, control of the display operation of the internal fixation target by the LCD 140, etc.

Further, for the OCT unit 150, the controller 210 performs control of the low-coherence light source 160 and the CCD 184, control of the density filter drive mechanism 244 for rotating the density filter 173, control of the reference-mirror driving mechanism 243 for moving the reference mirror 174 in the traveling direction of the reference light LR, etc.

Herein, the reference-mirror driving mechanism 243 functions as one example of the "driver" of the present invention. Moreover, the controller 210 functions as one example of the "controller" of the present invention.

Furthermore, the controller 210 performs control for causing the display 240A of the user interface (UI) 240 to display two kinds of images photographed by the fundus oculi observation device 1: that is, a 2-dimensional image of the surface of the fundus oculi Ef obtained by the retinal camera unit 1A, and a tomographic image of the fundus oculi Ef formed based on the detection signals obtained by the OCT unit 150. These images may be displayed on the display 240A separately, or may be displayed side by side simultaneously.

(Image Forming Part)

An image forming part 220 performs a process of forming image data of the fundus oculi image based on the video signals from the imaging devices 10 and 12 of the retinal camera unit 1A, and a process of forming image data of the tomographic images of the fundus oculi Ef based on the detection signals from the CCD 184 of the OCT unit 150.

In particular, in the image-forming process based on the detection signals from the OCT unit 150, the image forming part 220 forms a tomographic image within a predetermined frame. Herein, the frame refers to a frame that becomes the range of formation of an image. At the time of displaying an image, an image formed within the frame is to be displayed.

When the retinal camera unit 1A is moved in the x-direction or y-direction, an image formed within the frame changes in the surface direction of the fundus oculi Ef. Furthermore, when the reference mirror 174 is moved, namely, when the optical path length of the reference light LR is changed, the depth position of an image formed within the frame changes. Thus, by appropriately aligning the position of the retinal camera unit 1A or the position of the reference mirror 174, it is possible to form an image of the fundus oculi Ef at a desired position and depth within the frame.

The imaging forming part 220 comprises the imaging forming board 208 and the communication interface 209. In this specification, "image" may be identified with "image data" corresponding thereto.

Herein, the image forming part 220 (OCT-image forming board 208b) functions as one example of the "image forming part" of the present invention.

(Image Processor)

The image processor 230 applies various image processing and analysis process to image data of images formed by the image forming part 220. For example, the image processor 230 executes a process of forming image data of a 3-dimensional image of the fundus oculi Ef based on the tomographic images corresponding to the detection signal from the OCT unit 150, and various correction processes such as brightness correction and dispersion correction of the images.

Herein, image data of a 3-dimensional image is image data made by assigning pixel values to each of a plurality of voxels arranged 3-dimensionally, and is referred to as volume data, voxel data, and the like. When displaying an image based on volume data, the image processor 230 operates to apply a rendering process (such as volume rendering and MIP (Maximum Intensity Projection)) to this volume data and form image data of a pseudo 3-dimensional image seen from a specified viewing direction. On a display device such as the display 207, the pseudo 3-dimensional image based on the image data is displayed.

Furthermore, an analyzing part 231 is disposed to the image processor 230. The analyzing part 231 conducts analytical processes for alignment of a measurement position in the depth direction of the fundus oculi Ef and functions as an example of the "analyzer" in the present invention. The analyzing part 231 includes a signal-level calculator 232, a signal-level determining part 233, an image-position specifying part 234, and a movement-distance calculator 235. Hereinafter, each of these parts 232 through 235 will be described.

(Signal-Level Calculator)

The signal-level calculator 232 analyzes an image (OCT image) formed by the OCT-image forming board 208b of the image forming part 220 and calculates the signal level of the OCT image. As for the method of calculating the signal level of the image, it is possible to use any known method. The OCT image to become the subject for calculation of the signal level may be a 2-dimensional tomographic image, or may be a 1-dimensional image of the depth direction (to be described later). Herein, the signal level refers to the intensity of signal components included in the image data of an OCT image, and is the intensity of a component obtained after (at least part of) a noise component is removed from the image data of the OCT image. This signal component is a component in which morphology of the fundus oculi Ef has been reflected.

(Signal-Level Determining Part)

The signal-level determining part 233 determines the size relation by comparing the signal level value calculated by the signal-level calculator 232 with a predetermined threshold value. The threshold value is previously set and stored in a hard disk drive 204a or the like.

(Image-Position Specifying Part)

The image-position specifying part 234 analyzes the OCT image whose signal level is determined to be over the threshold value by the signal-level determining part 233, and finds the position of the predetermined partial image in the frame previously described. This partial image is, for example, an image corresponding to a predetermined depth position of the fundus oculi Ef. As the depth position, for example, of a plurality of layers composing the fundus oculi Ef (nerve fiber layer, photoreceptor layer, retinal pigment epithelium, etc.), a layer in which the pixel value (brightness value or the like) within the OCT image becomes the greatest.

The partial image specified by the image-position specifying part 234 is not limited to those described above but may also be an image equivalent to any layer among the plurality of layers composing the fundus oculi Ef. Moreover, it is possible to specify an image region equivalent to the surface of the fundus oculi Ef as the partial region described above.

(Movement-Distance Calculator)

The movement-distance calculator 235 calculates the distance of movement of the reference mirror 174 based on the position of the partial image specified by the image-position specifying part 234.

To explain more concretely, first, the movement-distance calculator 235 calculates the displacement between the position of a partial image within the frame obtained by the image-position specifying part 234 and a specific position within the frame. This specific position is previously set as the predetermined depth position within the frame. Furthermore, this specific position is set at a position within a frame where the measurement sensitivity in measurement for capturing an OCT image is relatively favorable.

Assuming a coordinate value of the depth direction (z-direction) of the specific position within the frame is z0 and a coordinate value of the specific position of the partial image is z, the movement-distance calculator 235 calculates displacement $\Delta z = z - z0$. This method is effective, for example, when the partial image is a 1-dimensional image or when the z coordinate values of the respective pixels composing a 2-dimensional partial image are the same.

On one hand, in a case in which the partial image is a 2-dimensional image and also includes a pixel of different z coordinate value, it is difficult to employ the above method. Moreover, in a case in which the partial image includes a plurality of 1-dimensional images, it is also difficult to employ the above method. Then, in these cases, for example, the displacement $\Delta z$ can be found by employing a method as follows.

First, a z coordinate value z1 of a specified pixel of the specified partial image is found, and this z coordinate value z1 is assumed to be a z coordinate value of the partial image. Then, $z1 - z0$ is calculated, and the result of this calculation is assumed to be the displacement $\Delta z$. Herein, as the above-described specified pixel, for example, a pixel with the maximum or minimum z coordinate value, a pixel with a medium z coordinate value (in the middle of the maximum and the minimum), and a pixel that becomes a center in a direction orthogonal to a depth direction may be used.

Another method may be to define the average value of the z coordinate values of a plurality of pixels composing a partial image as a z coordinate value of the partial image. For example, in a case in which a partial image composed of a plurality of 1-dimensional images (images of the depth direction to be described later) is taken into consideration, a pixel with the maximum pixel value is specified in each of the 1-dimensional images, and the average value of the z coordinate values of the specified plurality of pixels can be defined as a z coordinate value of the partial image.

After the displacement $\Delta z$ is calculated as described above, the movement-distance calculator 235 calculates the movement distance of the reference mirror 174 corresponding to this displacement $\Delta z$. The distance of z-direction within a frame is previously associated with the distance of the depth direction (z-direction) of the fundus oculi Ef. The movement-distance calculator 235 calculates the distance of the depth direction of the fundus oculi Ef that corresponds to the displacement $\Delta z$ within the frame, based on the association of the distances. In an optical image measurement device, an image of the fundus oculi Ef is captured at the almost the same depth position as the optical distance from the optical coupler 162 to the reference mirror 174. Therefore, the movement distance of the reference mirror 174 becomes equal to the distance of the depth direction of the fundus oculi Ef calculated by the movement-distance calculator 235.

The image processor 230 that operates as described above comprises the microprocessor 201, the RAM 202, the ROM 203, and the hard disk drive 204 (control program 204a).

(User Interface)

The user interface (UI) 240 comprises the display 240A and an operation part 240B. The display 240A is composed of a display device such as the display 207. Further, the operation part 240B is composed of an input device or an operation device such as the keyboard 205 and the mouse 206.

(Operation Panel)

The operation panel 3a of the retinal camera unit 1A will be described. The operation panel 3a is arranged on the platform 3 of the retinal camera unit 1A, for example.

The operation panel 3a is provided with an operating part used to instruct an operation for capturing a 2-dimensional image of the surface of the fundus oculi Ef, and an operating part used to instruct an operation for capturing a tomographic image of the fundus oculi Ef.

Placement of the operation panel 3a makes it possible to execute an operation for capturing a fundus oculi image Ef and an operation for capturing a tomographic image in the same manner as when operating a conventional retinal camera.

As shown in FIG. 6, the operation panel 3a is provided with, for example, a menu switch 301, a split switch 302, an imaging light amount switch 303, an observation light amount switch 304, a jaw holder switch 305, a photographing switch 306, a zoom switch 307, an image switching switch 308, a fixation target switching switch 309, a fixation target position adjusting switch 310, a fixation target size switching switch 311, and a mode switching knob 312.

The menu switch 301 is a switch operated to display a certain menu screen for a user to select and designate various menus (such as an imaging menu for imaging a 2-dimensional image of the surface of the fundus oculi Ef, a tomographic image and the like, and a setting menu for inputting various settings).

When this menu switch 301 is operated, the operation signal is inputted to the controller 210. The controller 210 causes the touch panel monitor 11 or the display 240A to display a menu screen, in response to the input of the operation signal. A controller (not shown) may be provided in the retinal camera unit 1A, whereby the controller causes the touch panel monitor 11 to display the menu screen.

The split switch 302 is a switch operated to switch the light on and off of the split bright line for focusing (e.g., see JP Patent laid-open No. H9-66031. Also referred to as split target, split mark and so on). The configuration for projecting this split bright line onto the eye E (split bright line projection part) is housed, for example, in the retinal camera unit 1A (not shown in FIG. 1).

When this split switch 302 is operated, the operation signal is inputted to the controller 210 (or the aforementioned controller inside the retinal camera unit 1A; the same hereinafter). The controller 210 projects the split bright line onto the eye E by controlling the split bright line projection part, in response to the input of this operation signal.

The imaging light amount switch 303 is a switch operated to adjust the emitted light amount of the imaging light source 103 (photographing light amount) depending on the state of the eye E (such as the degree of opacity of the lens). This imaging light amount switch 303 is provided with, for example, a photographing light amount increasing switch "+" for increasing the photographing light amount, a photographing light amount decreasing switch "−" for decreasing the photographing light amount, and a reset switch (a button in the middle) for setting the photographing light amount to a predetermined initial value (default value).

When one of the imaging light amount switches 303 is operated, the operation signal is inputted to the controller 210. The controller 210 controls the imaging light source 103 in response to the inputted operation signal and adjusts the photographing light amount.

The observation light amount switch 304 is a switch operated to adjust the emitted light amount (observation light amount) of the observation light source 101. The observation light amount switch 304 is provided with, for example, an observation light amount increasing switch "+" for increasing the observation light amount, and an observation light amount decreasing switch "−" for decreasing the observation light amount.

When one of the observation light amount switches 304 is operated, the operation signal is inputted to the controller 210. The controller 210 controls the observation light source 101 in response to the inputted operation signal and adjusts the observation light amount.

The jaw holder switch 305 is a switch to move the position of the jaw holder (not shown) of the retinal camera unit 1A. This jaw holder switch 305 is provided with, for example, an upward movement switch (upward triangle) for moving the jaw holder upward, and a downward movement switch (downward triangle) for moving the jaw holder downward.

When one of the jaw holder switches 305 is operated, the operation signal is inputted to the controller 210. The controller 210 controls a jaw holder movement mechanism (not shown) in response to the inputted operation signal and moves the jaw holder upward or downward.

The photographing switch 306 is a switch used as a trigger switch for capturing a 2-dimensional image of the surface of the fundus oculi Ef or a tomographic image of the fundus oculi Ef.

When the photographing switch 306 is operated in a state where a menu to photograph a 2-dimensional image is selected, the controller 210 that has received the operation signal controls the imaging light source 103 to emit photographing illumination light, and also causes the display 240A or the touch panel monitor 11 to display a 2-dimensional image of the surface of the fundus oculi Ef, based on the video signal outputted from the imaging device 10 having detected the fundus oculi reflection light.

On the other hand, when the photographing switch 306 is operated in a state where a menu to capture a tomographic image is selected, the controller 210 that has received the operation signal controls the low-coherence light source 160 to emit the low-coherence light L0, and also controls the Galvano mirrors 141A and 141B to scan the signal light LS. Moreover, the controller 210 causes the display 240A or the touch panel monitor 11 to display a tomographic image of the fundus oculi Ef formed by the image forming part 220 (and image processor 230), based on the detection signal outputted from the CCD 184 that has detected the interference light LC.

The zoom switch 307 is a switch operated to change the angle of view (zoom magnification) at the time of photographing of the fundus oculi Ef. Every time this zoom switch 307 is operated, the photographing angle is set alternately to 45 degrees and 22.5 degrees, for example.

When this zoom switch 307 is operated, the controller 210 that has received the operation signal controls a variable magnifying lens driving mechanism (not shown) to move the variable magnifying lens 124 in the optical axis direction of the imaging optical system 120, thereby changing the photographing angle of view.

The image switching switch 308 is a switch operated to switch displayed images. When the image switching switch 308 is operated in a state where a fundus oculi observation image (a 2-dimensional image of the surface of the fundus oculi Ef based on the video signal from the imaging device 12) is displayed on the display 240A or the touch panel monitor 11, the controller 210 having received the operation signal controls the display 240A or touch panel monitor 11 to display the tomographic image of the fundus oculi Ef.

On the other hand, when the image switching switch 308 is operated in a state where a tomographic image of the fundus oculi is displayed on the display 240A or the touch pane monitor 11, the controller 210 having received the operation signal controls the display 240A or the touch panel monitor 11 to display the fundus oculi observation image.

The fixation target switching switch 309 is a switch operated to switch the position of the internal fixation target displayed by the LCD 140 (i.e. the projection position of the internal fixation target on the fundus oculi Ef). By operating this fixation target switching switch 309, the display position of the internal fixation target can be switched, for example, among "fixation position to capture the image of the peripheral region of the center of the fundus oculi (fixation position for fundus oculi center imaging)," "fixation position to capture the image of the peripheral region of macula lutea (fixation position for macula lutea imaging)" and "fixation position to capture the image of the peripheral region of papilla (fixation position for papilla imaging)," in a circulative fashion.

In response to the operation signals from the fixation target switching switch 309, the controller 210 causes the LCD 140 to display the internal fixation target in different positions on the display surface thereof. The display positions of the internal fixation target corresponding to the above three fixation positions, for example, can be preset based on clinical data, or can be set for each eye or for each image photographing in advance.

The fixation target position adjusting switch 310 is a switch operated to adjust the display position of the internal fixation target. This fixation target position adjusting switch 310 is provided with, for example, an upward movement switch for moving the display position of the internal fixation target upward, a downward movement switch for moving it downward, a leftward movement switch for moving it leftward, a rightward movement switch for moving it rightward, and a reset switch for moving it to a predetermined initial position (default position).

Upon reception of the operation signal from either of these switches of the fixation target position adjusting switch 310, the controller 210 controls the LCD 140 to move the display position of the internal fixation target, in response to the operation signal.

The fixation target size switching switch 311 is a switch operated to change the size of the internal fixation target. When this fixation target size switching switch 311 is operated, the controller 210 that has received the operation signal controls the LCD 140 to change the display size of the internal fixation target. The display size of the internal fixation target can be switched, for example, between "normal size" and "enlarged size," alternately. As a result, the size of the projection image of the fixation target projected onto the fundus oculi Ef is changed. Upon reception of the operation signal from the fixation target position adjusting switch 311, the controller 210 controls the LCD 140 to change the display size of the internal fixation target, in response to the operation signal.

The mode switching knob 312 is a knob rotationally operated to select various photographing modes. The photographing modes are, for example, a fundus oculi photographing mode to photograph a 2-dimensional image of the fundus oculi Ef, a B-scan mode to perform B-scan of the signal light LS, and a 3-dimensional scan mode to scan with the signal light LS 3-dimensionally. In addition, the mode switching knob 312 may be configured so as to be capable of selecting a replay mode to replay and display a captured 2-dimensional image or tomographic image of the fundus oculi Ef. In addition, it may be configured so as to be capable of selecting a photographing mode to control so that the photographing of the fundus oculi Ef would be performed immediately after scanning of the signal light LS. Control of each part of the device for causing the fundus oculi observation device 1 to execute the operation corresponding to the each mode is executed by the controller 210.

Herein, the feature of control of scanning of the signal light LS by the controller 210, and the feature of processing to the detection signal from the OCT unit 150 by the image forming part 220 and the image processor 230 will be respectively described. An explanation regarding the process by the image forming part 220, etc., to the video signal from the retinal camera unit 1A will be omitted because it is the same as the conventional process.

Signal Light Scanning

Scanning of the signal light LS is performed by changing the positions (directions of the reflecting surfaces) of the Galvano mirrors 141A and 141B of the scan unit 141 in the retinal camera unit 1A. By controlling the mirror drive mechanisms 241 and 242 respectively to change the directions of the reflecting surfaces of the Galvano mirrors 141A and 141B respectively, the controller 210 scans the application position of the signal light LS on the fundus oculi Ef.

When the facing direction of the reflecting surface of the Galvano mirror 141A is changed, the signal light LS is scanned in the horizontal direction (x-direction in FIG. 1) on the fundus oculi Ef. Whereas, when the facing direction of the reflecting surface of the Galvano mirror 141B is changed, the signal light LS is scanned in the vertical direction (y-direction in FIG. 1) on the fundus oculi Ef. Further, by changing the facing directions of the reflecting surfaces of both the Galvano mirrors 141A and 141B simultaneously, it is possible to scan the signal light LS in the composed direction of the x-direction and y-direction. That is, by controlling these two Galvano mirrors 141A and 141B, it is possible to scan the signal light LS in any direction on the x-y plane.

Figure 8A:
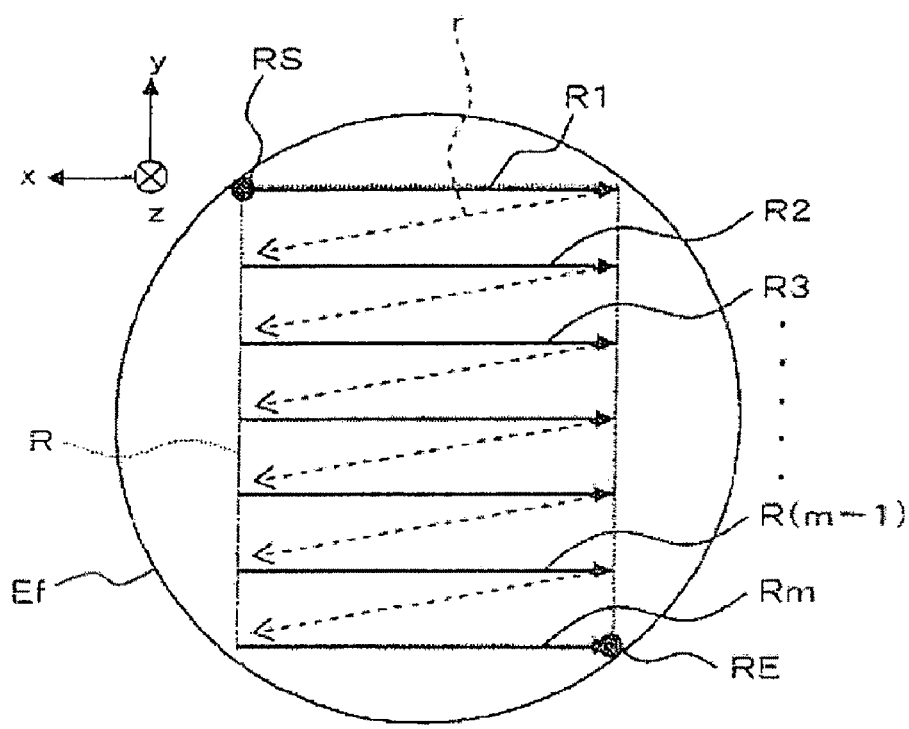
FIGS. 8A and 8B are schematic views showing one example of a scanning pattern of a signal light in the preferred embodiment of the device related to the present invention.
Figure 8B:
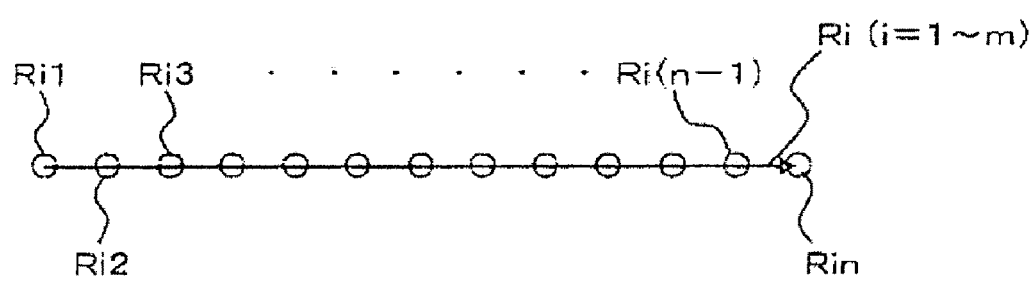

FIGS. 8A and 8B shows one example of the feature of scanning of the signal light LS for forming images of the fundus oculi. Ef. FIG. 8A shows one example of the feature of scanning of the signal light LS, when the fundus oculi Ef is seen from a direction that the signal light LS enters the eye E (that is, seen from −z side toward +z side in FIG. 1). Further, FIG. 8B shows one example of the feature of arrangement of scanning points (positions at which image measurement is carried out; target positions of the signal light LS) on each scanning line on the fundus oculi Ef.

As shown in FIG. 8A, the signal light LS is scanned within a rectangular-shaped scanning region R that has been preset. Within this scanning region R, a plurality of (m number of) scanning lines R1 through Rm are set in the x-direction. When the signal light LS is scanned along the respective scanning lines Ri (i=1 through m), detection signals of the interference light LC are generated.

Herein, a direction of each scanning line Ri will be referred to as the "main scanning direction" and a direction orthogonal thereto will be referred to as the "sub-scanning direction". Accordingly, scanning of the signal light LS in the main scanning direction is performed by changing the facing direction of the reflecting surface of the Galvano mirror 141A, and scanning in the sub-scanning direction is performed by changing the facing direction of the reflecting surface of the Galvano mirror 141B.

On each scanning line Ri, as shown in FIG. 8B, a plurality of (n number of) scanning points Ri1 through Rin are preset.

In order to execute the scanning shown in FIGS. 8A and 8B, the controller 210 firstly controls the Galvano mirrors 141A and 141B to set the target of the signal light LS entering into the fundus oculi Ef to a scan start position RS (scanning point R11) on the first scanning line R1. Subsequently, the controller 210 controls the low-coherence light source 160 to flush the low-coherence light L0, thereby making the signal light LS enter the scan start position RS. The CCD 184 receives the interference light LC based on the fundus oculi reflection light of this signal light LS at the scan start position RS, and outputs the detection signal to the controller 210.

Next, the controller 210 controls the Galvano mirror 141A to scan the signal light LS in the main scanning direction and set the incident target of the signal light LS to a scanning point R12, and makes the low-coherence light L0 flushed to make the signal light LS enter into the scanning point R12. The CCD 184 receives the interference light LC based on the fundus oculi reflection light of this signal light LS at the scanning point R12, and then outputs the detection signal to the controller 210.

Likewise, the controller 210 obtains detection signals outputted from the CCD 184 in response to the interference light LC for each scanning point, by flushing the low-coherence light L0 at each scanning point while shifting the incident target of the signal light LS from scanning point R13 to R14, - - - , R1 (n−1), and R1$n$ in order.

Once the measurement at the last scanning point R1$n$ of the first scanning line R1 is finished, the controller 210 controls the Galvano mirrors 141A and 141B simultaneously to shift the incident target of the signal light LS to the first scanning point R21 of the second scanning line R2 following a line switching scan r. Then, by conducting the previously described measurement on each scanning point R2$j$ (j=1 through n) of this second scanning line R2, detection signals corresponding to the respective scanning points R2$j$ are obtained.

Likewise, the measurement is conducted for each of the third scanning line R3, - - - , the m−1th scanning line R(m−1), the mth scanning line Rm to obtain the detection signals corresponding to the respective scanning points. Symbol RE on a scanning line Rm is a scan end position corresponding to a scanning point Rmn.

As a result, the controller 210 obtains m×n number of detection signals corresponding to m×n number of scanning points Rij (i=1 through m, j=1 through n) within the scanning region R. Hereinafter, a detection signal corresponding to the scanning point Rij may be represented by Dij.

Such interlocking control of the shift of scanning points and the emission of the low-coherence light L0 can be realized by synchronizing, for instance, timing for transmission of control signals to the mirror drive mechanisms 241 and 242 and timing for transmission of control signals (output request signals) to the low-coherence light source 160.

As described above, when each of the Galvano mirrors 141A and 141 B is operated, the controller 210 stores the position of each scanning line Ri and the position of each scanning point Rij (coordinates on the x-y coordinate system) as information representing the content of the operation. This stored content (scanning point coordinate information) is used in an image forming process as in conventional one.

Image Processing

Next, one example of a process on OCT images (tomography images of the fundus oculi Ef) by the image forming part 220 and the image processor 230 will be described.

The image forming part 220 executes the formation process of tomographic images of the fundus oculi Ef along each scanning line Ri (main scanning direction). Further, the image processor 230 executes the formation process of a 3-dimensional image of the fundus oculi Ef based on these tomographic images formed by the image forming part 220, etc.

The formation process of a tomographic image by the image forming part 220, as in the conventionally one, includes a 2-step arithmetic process. In the first step of the arithmetic process, based on a detection signal Dij corresponding to each scanning point Rij, an image in the depth-wise direction (z-direction in FIG. 1) of the fundus oculi Ef at the scanning point Rij is formed.

Figure 9:
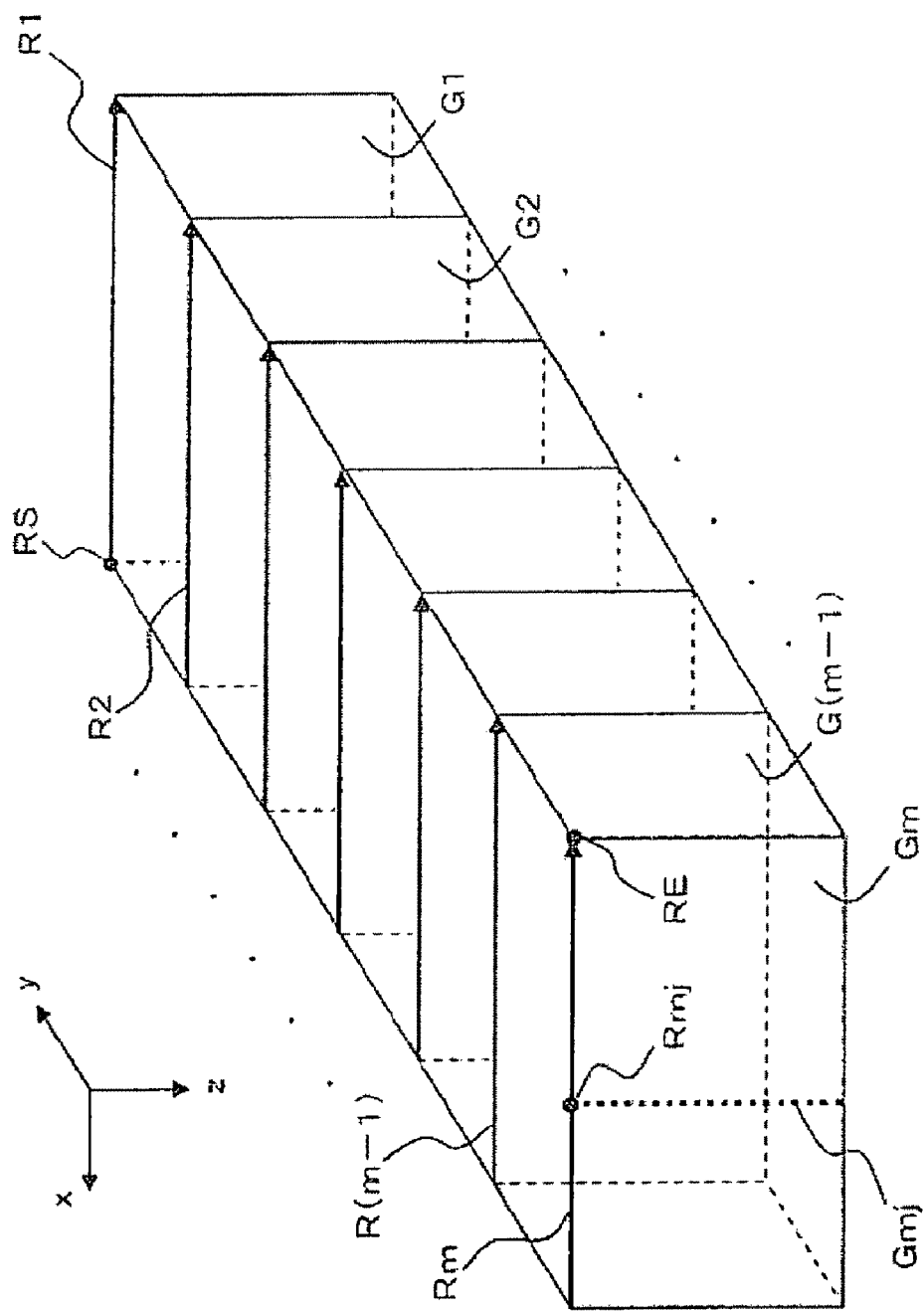
FIG. 9 is a schematic view showing one example of a scanning pattern of the signal light and a pattern of a tomographic image formed along each scanning line in the preferred embodiment of the device related to the present invention.

FIG. 9 shows a feature of (a group of) tomographic images formed by the image forming part 220. In the second step of the arithmetic process, on each scanning line Ri, based on the images in the depth-wise direction at the n number of scanning points Ri1 through Rin, a tomographic image Gi of the fundus oculi Ef along the scanning line Ri is formed. Then, the image forming part 220 determines the arrangement and the distance of the scanning points Ri1 through Rin referring to the positional information (scanning point coordinate information described before) of the scanning points Ri1 through Rin, and forms a tomographic image Gi along this scanning line Ri.

Through the above process, m number of tomographic images (a group of tomographic images) G1 through Gm at different positions in the sub-scanning direction (y-direction) are obtained.

Next, the formation process of a 3-dimensional image of the fundus oculi Ef by the image processor 230 will be explained. A 3-dimensional image of the fundus oculi Ef is formed based on the m number of tomographic images obtained through the above arithmetic process. The image processor 230 forms a 3-dimensional image of the fundus oculi Ef by performing a known interpolating process to interpolate an image between the adjacent tomographic images Gi and G (i+1).

Here, the image processor 230 determines the arrangement and distance of each scanning line Ri while referring to the positional information of each scanning line Ri to form this 3-dimensional image. For this 3-dimensional image, a 3-dimensional coordinate system (x,y,z) is set, based on the positional information (the scanning point coordinate information) of each scanning point Rij and the z-coordinate in the depth-wise image.

Furthermore, based on this 3-dimensional image, the image processor 230 can form a tomographic image of the fundus oculi Ef at a cross-section in any direction other than the main scanning direction (x-direction). Once the cross-section is designated, the image processor 230 determines the position of each scanning point (and/or an interpolated depth-wise image) on this designated cross-section, and extracts a depth-wise image at each determined position (and/or an interpolated depth-wise image), thereby forming a tomographic image of the fundus oculi Ef at the designated cross-section by arranging plural extracted depth-wise images.

Furthermore, an image Gmj shown in FIG. 9 represents an image in the depth-wise direction (z-direction) at the scanning point Rmj on the scanning line Rm. A depth-wise image at each scanning point Rij on the scanning line Ri formed by the first-step arithmetic process is represented as "image Gij."

[Usage Pattern]

Figure 10:
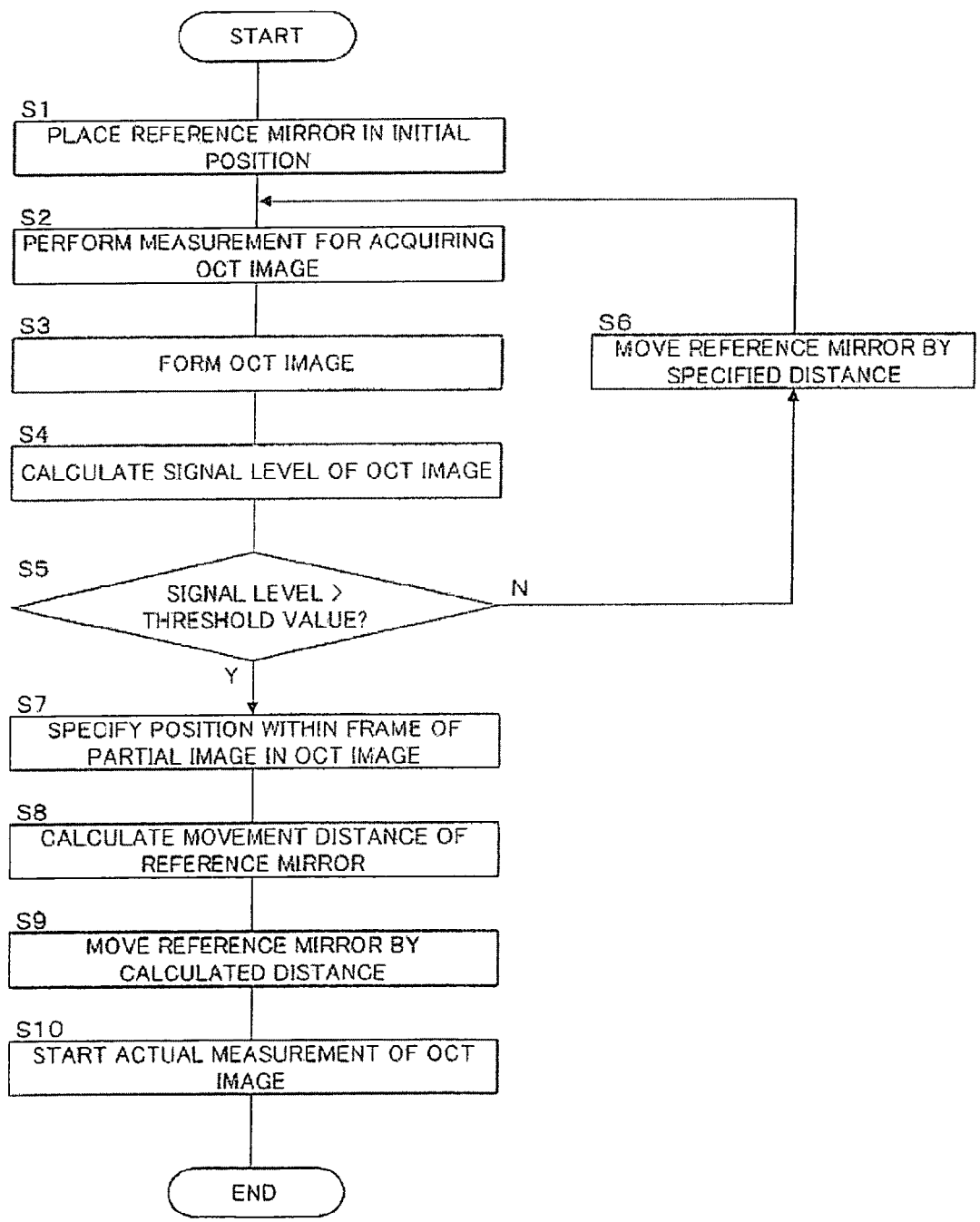
FIG. 10 is a flowchart showing one example of a usage pattern in the preferred embodiment of the device related to the present invention.

A usage pattern of the fundus oculi observation device 1 having the configuration as described above will be explained. A flowchart shown in FIG. 10 shows one example of the usage pattern of the fundus oculi observation device 1. The usage pattern shown in this flowchart is for automation of alignment of the measurement position in the depth direction of the fundus oculi Ef.

(Step 1)

First, the controller 210 controls the reference mirror driving mechanism 243 to place the reference mirror 174 at the predetermined initial position (S1). This initial position is previously set. In this embodiment, the reference mirror 174 is moved to a position where the optical path length of the reference light LR becomes the shortest. In other words, the reference mirror 174 is placed in the position closest to the optical coupler 162 within the movable range of the reference mirror 174.

(Step 2)

Next, measurement for capturing an OCT image is performed (S2). A specific example of this process will be described below. First, the controller 210 controls the low-coherence light source 160 to output the low-coherence light L0, and also controls the mirror driving mechanisms 241 and 242 to scan with the signal light LS. The reference light LR passed through the reference mirror 174 and the signal light LS passed through the fundus oculi Ef are superimposed by the optical coupler 162, whereby the interference light LC is generated. The interference light LC is split by the diffraction grating 182, and each spectrum is detected by the CCD 184. The CCD 184 transmits detection signals to the arithmetic control unit 200. This process is performed with respect to one scanning line Ri, for example (i.e., this process is performed with respect to n number of scanning points Ri1 to Rin).

(Step 3)

Subsequently, the image forming part 220 forms an OCT image based on the detection signals inputted from the CCD 184 (S3). At this time, it is possible to shorten the processing time by performing a process as described below, for example.

First, the image forming part 220 takes out detection signals at a predetermined number of scanning points from the n number of detection signals inputted from the CCD 184. The number of the detection signals to be taken out is determined beforehand, for example, to be approximately ten.

Furthermore, the image forming part 220 forms an image Gij (OCT image) of the depth direction based on the respective detection signals having been taken out. Consequently, the predetermined number of images of the depth direction can be captured.

(Step 4)

Next, the signal-level calculator 232 calculates the signal level of the OCT image formed by the image forming part 220

(S4). Then, the signal-level calculator 232 calculates, for example, the signal level of the image of each depth direction formed in Step 3.
(Step 5)

Next, the signal-level determining part 233 determines whether the signal level calculated by the signal-level calculator 232 exceeds a threshold value (S5). Then, the signal-level determining part 233 determines, for example, whether the signal level of an image of each depth direction calculated in Step 4 exceeds the threshold value, and determines as "Y" when the signal levels of all the depth images exceed the threshold value. The determination as "Y" may also be made when a predetermined number of signal levels exceed the threshold value among a plurality of images of the depth direction.

Herein, the fact that the signal level exceeds the threshold value is equivalent to the fact that a tomographic image of the fundus oculi Ef is included within a frame of the OCT image. On one hand, the fact that the signal level is equal to or less than the threshold value means that the image of the fundus oculi Ef is not included within the frame of the OCT image. Even in a case in which the tomographic image of the fundus oculi Ef is included within the frame of the OCT image, it is not clear at this stage whether this tomographic image is placed in a favorable position (e.g., a position with favorable measurement sensitivity) within the frame.
(Step 6)

When it is determined that the signal level is equal to or less than the threshold value in Step 5 (S5; N), the controller 210 controls the reference mirror driving mechanism 243 to move the reference mirror 174 by a specified distance (S6). The specified distance is set in advance.

In this embodiment, the position where the optical path length of the reference light LR becomes the shortest is the initial position of the reference mirror 174 (refer to Step 1), and therefore, the reference mirror 174 is moved in a manner that the optical path length of the reference mirror LR is longer by the specified distance.

When the reference mirror 174 is moved by the specified distance, the processing returns to S2, and the process up to Step 5 is executed again. Thus, until the result of determination at Step 5 becomes "Y," the process from Step 2 through Step 5 is repeated. In other words, until a tomographic image of the fundus oculi Ef shows up within the frame of the OCT image, such an action is made to gradually change the optical path length of the reference light LR by a specified distance.
(Step 7)

In a case where it is determined in Step 5 that the signal level exceeds the threshold value (S5; Y), the image-position specifying part 234 specifies the position within the frame of a predetermined partial image of each OCT image (S7).
(Step 8)

Subsequently, the movement-distance calculator 235 calculates the distance of movement of the reference mirror 174, based on the position within the frame of the partial image specified in Step 7 (S8).
(Step 9)

The controller 210 moves the reference mirror 174 by the movement distance calculated in Step 8 (S9). Thus, the depth position of the fundus oculi Ef equivalent to the partial image and the specific position within the frame coincide.
(Step 10)

When the movement of the reference mirror 174 in Step 9 is complete, the controller 210 controls the low-coherence light source 160, the mirror driving mechanisms 241, 242, and so on to measure the OCT image (tomographic image) of the fundus oculi Ef (S10). The process from Step 1 through Step 9 is preparation for capturing the OCT image of the fundus oculi Ef, and Step 10 is actual measurement of the OCT image. The explanation of the usage pattern related to this embodiment ends here.

Specific Example

A specific example of the usage pattern of the fundus oculi observation device 1 described thus far will be described with reference to FIG. 11 through FIG. 13.

Figure 11:
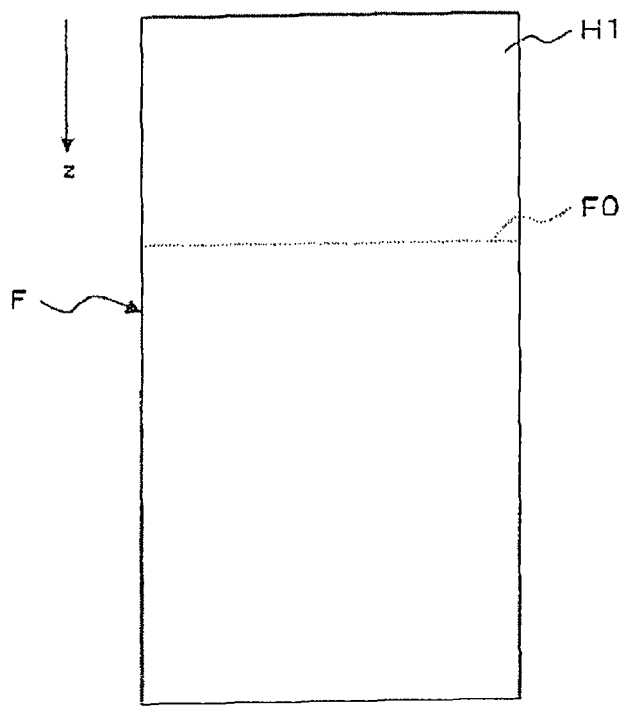
FIG. 11 is a schematic explanation view for explaining a specific example of the usage pattern in the preferred embodiment of the device related to the present invention.

When an OCT image is captured in a case where the determination result in Step 5 of the above usage pattern is "N," an OCT image H1 as shown in FIG. 11 is acquired. The OCT image H1 is formed within a frame F, but a tomographic image of the fundus oculi Ef is not included within the frame F. In this case, since the depth position corresponding to the position of the reference mirror 174 exists within the vitreous body, the tomographic image of the fundus oculi Ef does not show up within the frame F.

Reference symbol F0 in FIG. 11 denotes a specific position within the frame F described in the process for calculating the movement distance of the reference mirror 174. In the frame F shown in FIG. 11, measurement sensitivity is favorable on the side with a smaller z coordinate value (i.e., the upper side of the paper in FIG. 11). This is because the initial position of the reference mirror 174 corresponds to the side with a smaller z coordinate value as described in Step 1.

Figure 12:
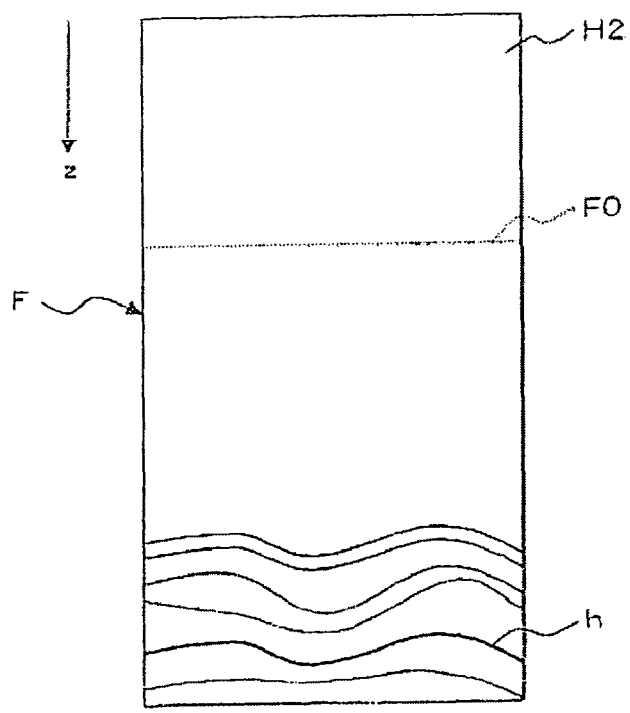
FIG. 12 is a schematic explanation view for explaining a specific example of the usage pattern in the preferred embodiment of the device related to the present invention.

When an OCT image is captured when the determination result in Step 5 is "Y," an OCT image H2 as shown in FIG. 12 is acquired. This OCT image H2 is formed within the frame F, and includes a tomographic image of the fundus oculi Ef in a region on a side where the z coordinate value within the frame F is greater (i.e., lower side of the paper in FIG. 12). Reference symbol h within FIG. 12 denotes a layer of the fundus oculi Ef equivalent to the above-described partial image with the greatest pixel value.

The OCT image H2 shown in FIG. 12 includes the tomographic image of the fundus oculi Et but this tomographic image is displayed in a region within the frame F where measurement sensitivity is not favorable. In the above usage pattern, a tomographic image is to be displayed in a region within the frame F with favorable measurement sensitivity by the process from Step 7 through Step 9.

That is to say, the position within the frame F of a partial image equivalent to the layer h of the OCT image H2 is specified in Step 7, and the movement distance of the reference mirror 174 is found in Step 8 by calculating the displacement between the z coordinate value of the layer h and the z coordinate value of the specific position F0. Then, in Step 9, the reference mirror 174 is moved by the movement distance.

Figure 13:
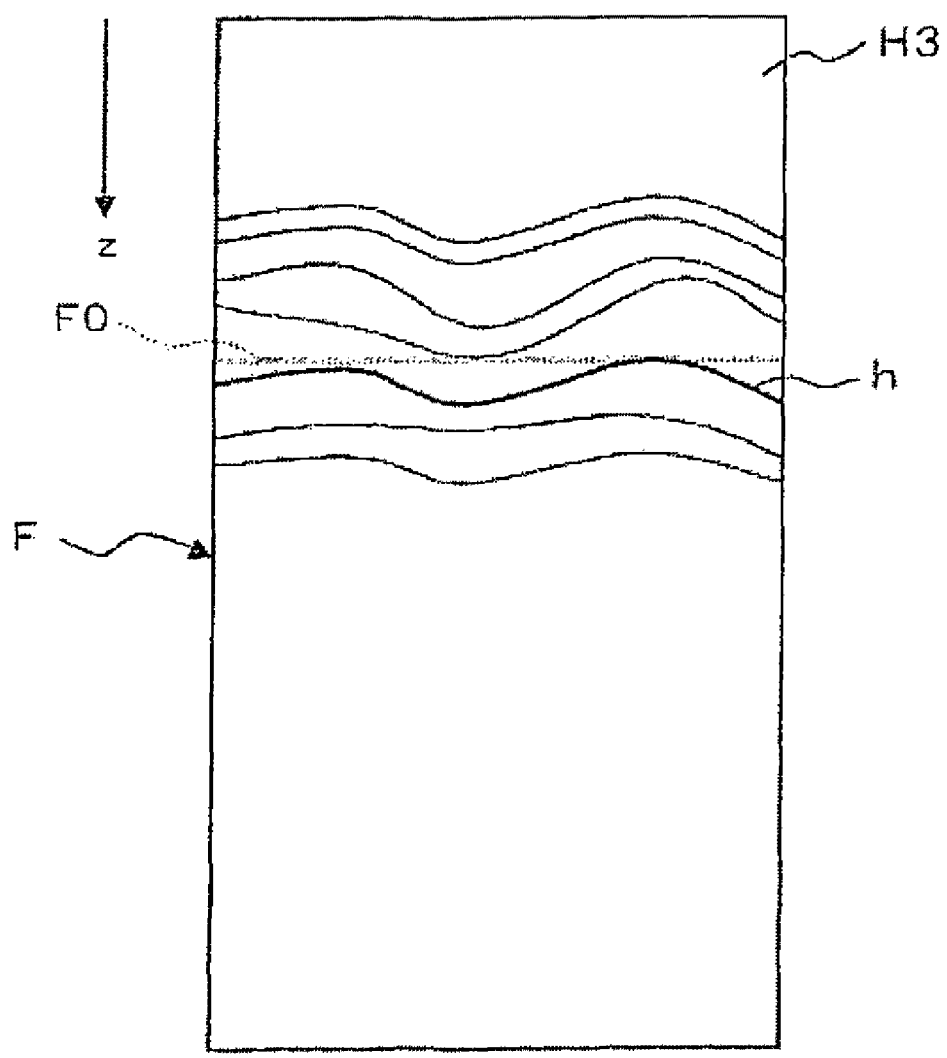
FIG. 13 is a schematic explanation view for explaining a specific example of the usage pattern in the preferred embodiment of the device related to the present invention.

By conducting such a process, a tomographic image of the fundus oculi Ef is displayed in a manner that the layer h is placed in the specific position F0 within the frame F, like an OCT image H3 shown in FIG. 13. As described above, the specific position F0 is set in a position within the frame F where the measurement sensitivity is favorable. Therefore, the tomographic image in the OCT image H3 is clearly displayed in comparison with the tomographic image within the OCT image H2 of FIG. 12.

Actions and Advantageous Effects

Actions and advantageous effects of the fundus oculi observation device 1 as described above will be described below.

The fundus oculi observation device 1 acts as an optical image measurement device capable of measuring an OCT image such as a tomographic image of the fundus oculi Ef, or the like, and is configured so as to calculate the signal level of the formed OCT image, determine whether the signal level exceeds a threshold value, and change the position of the reference mirror 174 so that the signal level is determined to exceed the threshold value.

Since the fundus oculi observation device 1 acts so as to change the position of the reference mirror 174 so that the signal level of an OCT image to be formed becomes greater than the threshold value, it is possible to automatically capture such an OCT image that includes a tomographic image of the fundus oculi Ef within a frame. Thus, according to the fundus oculi observation device 1, it is possible to easily align the measurement position in the depth direction of the fundus oculi Ef (measurement subject).

In particular, since the fundus oculi observation device 1 is configured so as to search the position of the reference mirror 174 where the signal level exceeds the threshold value by sequentially changing the optical path length of the reference light LR by a specified distance from the initial position until the tomographic image of the fundus oculi Ef shows up within the frame, it is possible to securely find the favorable measurement position in the depth direction of the fundus oculi Ef.

Furthermore, since the fundus oculi observation device 1 is configured so as to change the position of the reference mirror 174 so that a predetermined, partial image of an image whose signal level is determined to exceed the threshold value is placed in a specific position within the frame, it is possible to easily capture an OCT image in which the tomographic image of the fundus oculi Ef is placed in the vicinity region of the specific position within the frame. By setting a position with favorable measurement sensitivity as the specific position when measuring an OCT image, it is possible to easily capture a clear tomographic image of the fundus oculi Ef.

The actions and advantageous effects described above are exerted when a tomographic image of the fundus oculi Ef is not included within a frame at an initial stage. On one hand, when the tomographic image of the fundus oculi Ef is included within the frame, such as when a tomographic image of the fundus oculi Ef is included within the frame of an OCT image at an initial stage, the fundus oculi observation device 1 has the following characteristics. That is to say, the fundus oculi observation device 1 functions to change the position of a reference mirror 174 so that a partial image equivalent to a predetermined depth position of the fundus oculi Ef is placed in a specific position within the frame. According to such a fundus oculi observation device 1, an OCT image in which a tomographic image of the fundus oculi Ef is placed in the vicinity region of the specific position within a frame can be easily acquired, so it is possible to easily align the measurement position in the depth direction of the fundus oculi Ef.

In the present invention, a difference in optical path length between a signal light and a reference light is changed in a manner that the signal level or the ratio of the signal level and the noise level of an image exceeds a threshold value, so that an image including an image of a measurement subject can be automatically captured. Therefore, according to the present invention, it is possible to easily align the measurement position in the depth direction of the measurement subject.

Further, in the present invention, the difference in optical path length between the signal light and the reference light is changed in a manner that a partial image corresponding to a predetermined depth position of the measurement subject is located in a specific position within a frame, so that an image in which an image of the measurement subject is located in the vicinity region of the specific position within the frame can be automatically captured. Therefore, according to the present invention, it is possible to easily align the measurement position in the depth direction of the measurement subject.

[Modification]

The configuration described above is merely a specific example for favorably implementing the present invention. Therefore, it is possible to properly make any modification within the scope and intent of the present invention.

For example, in the embodiment described above, the difference between the light path of a signal light and the light path of a reference light (difference in optical path length) is changed by changing the position of the reference mirror 174, but the method for changing the difference in optical path length is not limited to this. For instance, it is possible to change the difference in optical path length by integrally moving the retinal camera unit 1A and the OCT unit 150 with respect to the eye E and changing the optical path length of the signal light LS. Furthermore, it is also possible to change the difference in optical path length by moving a measurement subject in a depth direction (z-direction). In general, as the "changer" in the present invention, it is possible to employ any constitution for changing the difference in optical path length between the signal light and reference light.

Moreover, in the embodiment described above, a state where the optical path length of the reference light is shortest is assumed to be an initial state and a state where the signal level exceeds the threshold value is searched, but it is also possible to configure so that any state such as a state where the light path length of the reference light is the longest is assumed to be an initial state and a target state is searched.

Furthermore, in the embodiment described above, a state where the signal level exceeds the threshold value is searched while gradually increasing the optical path length of the reference light, but it is also possible to configure so that the target state is searched while gradually decreasing the optical path length of the reference light. Moreover, it is also possible to configure so as to pursue the target state by increasing and decreasing the optical path length of the reference light. In addition, instead of changing the optical path length of the reference light, it is also possible to configure so as to search the target state by gradually increasing (or decreasing) the optical path length of the signal light or pursue the target state by increasing and decreasing the optical path length of the signal light.

Moreover, in the embodiment described above, the position of an image of the measurement subject within a frame is determined based on the signal level of an OCT image, but it is also possible to configure so that the position of the image is determined based on the ratio of signal level and noise level (S/N ratio).

Calculation of the S/N ratio of an OCT image is conducted by an analyzing part 231 (analyzer). Furthermore, it is possible to employ any known method as a method for calculating the S/N ratio. Moreover, the OCT image to be subjected to calculation of the S/N ratio may be a 2-dimensional tomographic image, or may be a 1-dimensional image of a depth direction.

By thus considering the S/N ratio, it is possible to increase the accuracy in determining the image position. In particular, it may be desired to consider the S/N ratio, for example, when the amount of noise contained in an OCT image is large or noise cannot be removed effectively due to the state of the measurement subject or the device.

The fundus oculi observation device described in the above embodiment is comprises an optical image measurement device of Fourier domain type, but it is also possible to apply the configuration of the present invention to an optical image measurement device of Time Domain type. The time domain type of optical image measurement device is described in, for example, Japanese Unexamined Patent Application Publication 2005-241464. Moreover, it is also possible to apply the configuration of the present invention to an optical image measurement device of any other type such as a Swept Source type.

[Program]

A program configured to control the device according to the present invention will be explained hereunder. In the above embodiments, the control program 204*a* is equivalent to the program.

This program is a computer program for controlling an optical image measurement device having: a light source for outputting a low-coherence light; an interference-light generator for generating an interference light by splitting the outputted low-coherence light into a signal light heading toward a measurement subject and a reference light heading toward a reference object, and superimposing the signal light passed through the measurement subject and the reference light passed through the reference object; a changer for changing the difference in optical path length between the signal light and the reference light; a detector for detecting the interference light; and an image forming part for forming an image based on the detection result, whereby: the optical image forming device is caused to function as an analyzer that analyzes the image formed by the image forming part, calculates a signal level or the ratio of a signal level and a noise level of the image and determines whether the calculated signal level or ratio of the signal level and the noise level exceeds a threshold value; and the optical image forming device is caused to function as a controller for controlling the changer and changes the difference in optical path length so that the analyzer determines that the signal level or the ratio of the signal level and the noise level exceeds the threshold value.

This program is configured so as to change the difference in optical path length between the signal light and the reference light so that the signal level or the ratio of the signal level and the noise level of an image exceeds the threshold value, whereby it is possible to automatically capture an image including the image of the measurement subject. Thus, according to this program, it is possible to easily align the measurement position of the measurement subject in the depth direction.

Furthermore, this program is a computer program for controlling an optical image measurement device having: a light source for outputting a low-coherence light; an interference-light generator for generating an interference-light by splitting the outputted low-coherence light into a signal light heading toward a measurement subject and a reference light heading toward a reference object, and superimposing the signal light passed through the measurement subject and the reference light passed through the reference object; a changer for changing the difference in optical path length between the signal light and the reference light; a detector for detecting the interference-light; and an image-forming part for forming an image within a predetermined frame based on the detection results, whereby the optical image-forming device is caused to function as a controller for controlling the changer and changing the difference in optical path length so that a partial image equivalent to a predetermined depth position of the measurement subject in the image formed by the image forming part is placed in a specific position within the frame.

This program is configured so as to change the difference in optical path length between the signal light and the reference light so that the partial image equivalent to the predetermined depth position of the measurement subject is placed in the specific position within the frame, whereby an image in which an image of the measurement subject is placed in the vicinity region of the specific position within the frame can be taken out automatically. Thus, according to this program, it is possible to easily align the measurement position in the depth direction of the measurement subject.

This program can be stored in any recording medium readable by a drive of the computer. For example, a storing medium such as an optical disk, a magneto-optical disk (CD-ROM, DVD-ROM, DVD-ROM, MO, etc.) and a magnetic storing medium (hard disk, Floppy Disk™, ZIP, etc.) can be used. Moreover, it is also possible to store the program in a storage device such as a hard disk drive or a memory. Furthermore, it is also possible to transmit the program via a network such as the Internet and a LAN.

What is claimed is:

1. An optical image measurement device comprising:
   a light source configured to emit a low-coherence light;
   an interference-light generator configured to generate a interference light by splitting the emitted low-coherence light into a signal light heading toward a measurement subject and a reference light heading toward a reference object, and superimposing the signal light passed through the measurement subject and the reference light passed through the reference object;
   a changer configured to change a difference in optical path length between the signal light and the reference light;
   a detector configured to detect the generated interference light;
   an image forming part configured to form an image within a predetermined frame defined by a length in the depth-wise direction of the measurement object based on the result of the detection by the detector;
   a determination part configured to determine a positional relation between a predetermined depth position of the measurement subject in the formed image and a specific position within the predetermined frame; and
   a controller configured to control the changer to change the difference in optical path length so that a partial image corresponding to a predetermined depth position of the measurement subject in the formed image is placed in a specific position within the predetermined frame based on the determined positional relation,
   wherein the predetermined frame indicates a target region of forming the image based on the detection of the interference light; and
   the specific position within the frame indicates a region with favorable measurement sensitivity for the imaging based on the detection of the interference light.

2. The optical image measurement device according to claim 1, wherein:
   the reference object is a mirror reflecting the reference light; and
   the changer includes a driver moving the mirror in a traveling direction of the reference light.

* * * * *